US006352863B1

(12) United States Patent
Guirguis

(10) Patent No.: US 6,352,863 B1
(45) Date of Patent: *Mar. 5, 2002

(54) ASSAY DEVICE

(75) Inventor: Raouf A. Guirguis, Rockville, MD (US)

(73) Assignee: La Mina, Inc., Arlington, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/788,343

(22) Filed: Jan. 27, 1997

Related U.S. Application Data

(63) Continuation of application No. 08/484,845, filed on Jun. 7, 1995, now abandoned, which is a continuation of application No. 08/123,077, filed on Sep. 17, 1993, now abandoned, which is a continuation-in-part of application No. 08/118,268, filed on Sep. 9, 1993, now abandoned, which is a continuation of application No. 07/759,922, filed on Sep. 13, 1991, now Pat. No. 5,244,815, which is a continuation-in-part of application No. 07/668,115, filed on Mar. 12, 1991, now abandoned, which is a continuation-in-part of application No. 07/467,532, filed on Jan. 19, 1990, now abandoned.

(51) Int. Cl.[7] ............................................. G01N 33/546

(52) U.S. Cl. ........................... 436/534; 422/56; 422/58; 422/60; 435/13; 435/7.92; 435/970; 435/975; 436/518; 436/169; 436/525; 436/530; 436/531; 436/536; 436/538; 436/541; 436/808; 436/810; 436/815; 436/816; 436/901

(58) Field of Search ............................... 422/56, 58, 60; 435/13, 970, 7.92, 975; 436/518, 525, 530, 531, 534, 536, 538, 541, 169, 808, 810, 815, 816, 901

(56) References Cited

U.S. PATENT DOCUMENTS

| 3,784,358 | A |   | 1/1974  | Drake, Jr. |
| 4,632,901 | A |   | 12/1986 | Valkirs et al. ................. 435/5 |
| 4,717,656 | A |   | 1/1988  | Swanljung ................... 435/7.9 |
| 4,774,192 | A |   | 9/1988  | Terminiello et al. ........ 436/530 |
| 4,775,636 | A |   | 10/1988 | Moeremans et al. ........ 436/518 |
| 4,810,630 | A |   | 3/1989  | Craig et al. ................. 435/7.9 |
| 4,826,759 | A | * | 5/1989  | Guire et al. ................... 435/4 |
| 4,853,335 | A |   | 8/1989  | Olsen et al. ................ 436/527 |

(List continued on next page.)

FOREIGN PATENT DOCUMENTS

| EP | 0200381 | 11/1986 |
| EP | 0203238 | 12/1986 |
| EP | 0440350 | 8/1991  |

OTHER PUBLICATIONS

John P. Nielson et al., "A Processing Protocol For Drug Residue And Latent Print Evidence", Journal Of Forensic Sciences, JFSCA, vol. 33, No. 6, Nov. 1988, pp. 1463–1472.
The Fisher Catalog, Fisher Scientific, 1990.

(List continued on next page.)

Primary Examiner—Christopher L. Chin
(74) Attorney, Agent, or Firm—Rothwell, Figg, Ernst & Manbeck

(57) ABSTRACT

An assay device and method are provided which allow the determination of the presence or absence of at least one analyte in a test sample, while providing specific identification of the test subject. The assay device includes a reaction medium having at least one reaction zone and at least one control zone, which is capable of providing a pattern suitable for identifying the test subject. The pattern suitable for identifying the test subject is preferably a fingerprint. In a preferred embodiment of the invention, the reaction zone and the control zone include at least one member of a ligand/receptor pair.

79 Claims, 9 Drawing Sheets

U.S. PATENT DOCUMENTS

| | | | | |
|---|---|---|---|---|
| 4,883,764 A | | 11/1989 | Kloepfer | 436/63 |
| 4,959,324 A | * | 9/1990 | Ramel et al. | 436/169 |
| 4,963,325 A | | 10/1990 | Lennon et al. | 422/61 |
| 5,006,464 A | | 4/1991 | Chu et al. | 435/7.1 |
| 5,028,535 A | | 7/1991 | Buechler et al. | 435/7.1 |
| 5,071,746 A | * | 12/1991 | Wilk et al. | 435/7.94 |
| 5,079,029 A | | 1/1992 | Sauders | 427/1 |
| 5,079,172 A | | 1/1992 | Hari et al. | 436/518 |
| 5,104,619 A | | 4/1992 | de Castro et al. | 422/56 |
| 5,221,627 A | * | 6/1993 | Grigg et al. | 436/89 |
| 5,244,815 A | | 9/1993 | Guirguis | 436/530 |
| 5,270,167 A | * | 12/1993 | Francoeur | 435/7.21 |
| 5,308,580 A | | 5/1994 | Clark | 422/58 |
| 5,342,645 A | * | 8/1994 | Eisele et al. | 427/1 |
| 5,378,492 A | * | 1/1995 | Mashiko | 427/1 |
| 5,416,000 A | * | 5/1995 | Allen et al. | 435/7.92 |
| 5,468,648 A | * | 11/1995 | Chandler | 436/518 |
| 5,629,164 A | * | 5/1997 | Rivers | 435/7.9 |
| 5,869,345 A | * | 2/1999 | Chandler | 436/514 |
| 5,876,926 A | * | 3/1999 | Beecham | 435/5 |

OTHER PUBLICATIONS

Richard Leute, PhD et al., "Spin Immunoassay of Opiate Narcotics in Urine and Saliva", JAMA The Journal Of The American Medical Association, vol. 221, No. 11, Sep. 11, 1972, pp. 1231–1234.

Harold W. Peel et al., "Detection Of Drugs in Saliva Of Impaired Drivers", Journal Of Forensic Sciences, JFSCA, vol. 29, No. 1, Jan. 1984, pp. 185–189.

O.R. Idowu et al., "A Review Of The Use Of Saliva In The Forensic Detection Of Drugs And Other Chemicals", JFSS Commentary, Journal Of The Forensic Sciences Society 1982, vol. 22, pp. 123–135.

Loren K. Thompson et al., "Confirmation Of Cocaine In Human Saliva After Intravenous Use", *Journal Of Analytical Toxicology*, vol. 11, Jan./Feb. 1987, pp. 36–38.

"Secretion", Chapter 44, General Considerations, pp. 680–695.

Edward J. Cone et al., "Prolonged Occurrence Of Cocaine In Human Saliva And Urine After Chronic Use", *Journal Of Analytical Toxicology*, vol. 13, Mar./Apr. 1989, pp. 65–68.

Eugene D. Jacobson, "Salivary Secretion", *Gastrointestinal Physiology*, Chapter 6, pp. 46–54.

Schramm et al., "An Ultrafiltrate of Saliva Collected in Situ As A Biological Sample For Diagnostic Evaluation", *Clinical Chemistry*, vol. 37, No. 1, 1991, pp. 114–115.

Edward J. Cone et al., "Stability Of Cocaine In Saliva", *Clinical Chemistry*, vol. 34. No. 7, 1988, p. 1508.

Wolff et al., "Methadone In Saliva", *Clinical Chemistry*, vol. 37, No. 7, 1991, pp. 1297–1298.

Sasaki Akira et al., "Ink–Free Fingerprint Recording Films", The American Chemical Society, *Chemical Abstracts*, vol. 108, No. 8, Feb. 22, 1988, p. 66.

G.G. Graham, "Noninvasive Chemical Methods Of Estimating Pharmacokinetic Parameters", Pharmac. Ther. vol. 18, 1982, pp. 333–349.

W.A. Ritschel et al., "Monitoring Of Drug Concentrations In Saliva: A Non–Invasive Pharmacokinetic Procedure", 1983, *Exptl. Clin. Pharmacol*, vol. 5, pp. 511–525.

Charles W. Gorodetzky et al., "Validity Of Screening Methods For Drugs of Abuse In Biological Fluids", Jan. 14, 1974, Clinical Pharmacology And Therapeutics, pp. 579–587.

Edward J. Cone, "Testing Human Hari For Drugs Of Abuse. I. Individual Dose And Time Profiles Of Morphine and Codeine In Plasma, Saliva, Urine, And Beard Compared To Drug–Induced Effects On Pupils And Behavior", *Journal Of Analytical Toxicology*, vol. 14, Jan./Feb. 1990, pp. 1–7.

Edward J. Cone et al., "Correlation Of Saliva Cocaine Levels With Plasma Levels And With Pharmacologic Effects After Intravenous Cocaine Administration In Human Subjects", *Journal Of Analytical Toxicology*, vol. 12, Jul./Aug. 1988, pp. 200–206.

* cited by examiner

ASSAY DEVICE

This application is a continuation application of U.S. Ser. No. 08/484,845, filed Jun. 7, 1995, now abandoned; which is a continuation application of U.S. Ser. No. 08/123,077, filed Sep. 17, 1993, now abandoned; which is a continuation-in-part application of U.S. Ser. No. 08/118,268 filed Sep. 9, 1993, now abandoned; which is a continuation application of U.S. Ser. No. 07/759,922, filed Sep. 13, 1991, now U.S. Pat. No. 5,244,815; which is a continuation-in-part application of U.S. Ser. No. 07/668,115, filed Mar. 12, 1991, now abandoned; which is a continuation-in-part application of U.S. Ser. No. 07/467,532, filed Jan. 19, 1990, now abandoned.

TECHNICAL FIELD OF THE INVENTION

The invention is in the field of ligand-receptor assays, including immunoassays, used for determining the presence or absence of an analyte in a biological fluid. More particularly, the apparatuses and methods of the invention relate to establishing the identity of a test subject and determining the presence or absence of at least one analyte in a biological fluid taken from the test subject using a single test device.

BACKGROUND OF INVENTION

For many years, those skilled in the art of ligand-receptor assays have sought an effective, inexpensive, and reliable device and method for detecting the presence and/or absence of antigens, antibodies, and the like. The art is replete with such devices.

For many years, those skilled in the art have also sought devices and methods for assuring that the sample being tested actually came from a certain individual. Many schemes, some elaborate, some simple, have been established to verify that the test sample was in fact produced by a particular individual. Similarly, many schemes exist to thwart matching a particular test result with a particular person.

For example, drug testing is now a routine procedure in athletics, prison, and the work place. The protocols involve testing individual fluid samples such as urine or blood to determine the presence of certain antibodies in the fluid sample; a positive result may be an indication of drug use.

Previously such testing has been accomplished by a series of tests which may involve shifting of the fluid being tested to different containers and removal of the fluid from the person being tested to a distant place. Oftentimes, fluid misplacement and/or substitution opened questions as to the chain of custody of the tested fluid. Thus, a problem which has occurred during such testing is that test fluids may be obtained from persons other than the person to be tested or that test fluids become mixed, lost, or cannot be specifically identified with that person after the test is returned from the laboratory. Also, these assays typically take too long to obtain timely results.

Other shortcomings are associated with many of the devices and methods currently used for the determination of analytes in biological fluids. Frequently, a certain level of skill is required to use or handle such devices to obtain satisfactory results. In addition, most of these devices require one or more additional reagents, and frequently a wash solution, to apply to the device during the course of the test. In many of these devices, due at least in part to the limited sensitivity of the devices, relatively large amounts of oftentimes expensive reagents or of test sample are required to give accurate results.

As noted above, the principles which form the basis for this type of detection is a person's immune system, i.e., the inherent capability of a mammal to respond to a foreign molecule, typically a macromolecule. Hereinafter, any molecule which is capable of eliciting such a response will be referred to as an antigen, i.e., an antibody generator. The proteins and protein fragments which are produced in response to the antigen will be referred to as antibodies or immunoglobulins.

SUMMARY OF THE INVENTION

The present invention overcomes problems inherent in known assay devices and systems through the use of a specifically designed assay device, preferably an immunoassay device which allows the determination of the presence or absence of an analyte in a sample, and preferably specifically identifies the person providing the sample.

The present invention is directed to a testing method and device and more specifically to a method and device for detecting the presence of an analyte, most preferably specific antigens or specific antibodies in a biological fluid. The present invention preferably also provides for positively identifying the individual tested.

The present invention provides an easily handled, disposable testing pad and a disposable test device suitable for detecting the presence or absence of an analyte and preferably for identifying the test subject. For example, a finger of the test subject may be coated with a labelled ligand and the finger may be pressed on a membrane substrate having a specific immobilized ligand bed to capture an analyte from a biological fluid while simultaneously providing an inkless (specific binding) visible fingerprint of the test subject so that positive identification of the fluid donor is irrefutably obtained. The fingerprint of the fluid donor obtained on the membrane may also include information about analytes, such as drugs, present in his body fluids at the time of performing the test. This information can be recorded or stored for positive identification when needed.

It is an object of the invention to assay a test sample for the presence or absence of an analyte while also identifying the subject being tested. Thus, problems of misidentification, chain of title, and delays may be eliminated.

It is an object of the present invention to provide a device for rapidly determining the presence or absence of an analyte taken from a test subject. It is also an object of the present invention to provide a device for rapidly determining the quantitative amount of an analyte in a sample taken from a test subject. Yet other objects of the present invention are to provide a device and a method of determining the presence or absence of a drug or drug metabolite in a test sample taken from a test subject and to provide a device and method determining whether a test subject is an acute or chronic drug abuser.

Another embodiment of the present invention, where identifying the test subject by a fingerprint is not critical, involves applying the sample of body fluid or a labelled ligand to the membrane with the pressure of a transfer means or applicator that is part of the test device. In contrast to similar known devices which apply liquid test samples and/or reagents dropwise to the surface of a reaction medium, the present invention, in which liquid test samples and/or reagents are applied and maintained under pressure on the surface of the reaction medium for a short duration, requires smaller amounts of test sample and reagents and demonstrates higher sensitivities than known devices.

A device according to the present invention which uses this principle is an enclosed assay test device. A preferred embodiment is one in which the assay test device includes a housing, a reaction medium having at least one reaction zone located in the housing, a medium containing a signal-producing or analyte-indicating agent located in the housing, and a medium for containing a test sample located in the housing. Both the medium containing a signal-producing agent and the medium for containing a test sample located in the housing are movable independently between a first position in spaced relationship to the reaction medium and a second position in substance-transferrable contact with the reaction medium. Preferably this is a self-contained test device.

A particular embodiment of this invention includes an assay test device employing a two-part housing. In one embodiment of the device, a reaction medium having at least one reaction zone is mounted in a first part of the housing. In the second part of the two-part housing is located a medium for containing a portion of a test sample. The medium for containing a portion of a test sample and the reaction medium are so arranged in the two parts of the housing that when the housing parts are brought together in a closed relationship, there is substance transferrable contact between the medium for containing a portion of a test sample and the reaction medium. In addition to at least one reaction zone, the reaction medium preferably has a control zone which is provided to identify the test subject by a fingerprint or like means if desired. Such a device may be designed as a self-contained assay device. As used herein, the term "self-contained" means that the device may be used without the addition of additional reagents or solutions, or only requiring the dropwise addition of water.

Another embodiment employs a somewhat similar arrangement but a medium containing a signal-producing agent is substituted for the medium for containing a portion of a test sample.

A preferred device according to the above "pressure" principle is similar to the aforementioned devices in that a two-part housing is also employed in which a reaction medium having at least one reaction zone is mounted in a first part of the two-part housing. However, like one of these embodiments, in the second part of the two-part housing, there is located a medium containing a signal-producing agent, such as a labelled material which will indicate the presence of an analyte. The device also includes a removable medium for containing a portion of a test sample which is located intermediate the first and second parts of the housing and in substance-transferable contact with the reaction medium when the first and second parts of the housing are in a closed relationship in a first closed position of the housing. The reaction medium and medium containing an analyte-indicating agent (or signal-producing agent) are so positioned and arranged within their separate housing parts that when the parts of the housing are in a closed relationship in a second position, the reaction medium and means for transferring the analyte-indicating agent are in substance transferable contact with one another.

In using this device, a test sample drawn from a test subject is placed on a removable medium for containing and transferring a portion of a test sample which is placed in the two-part housing. The housing is then closed to a first position such that the removable test sample containing medium is in transferable contact with and applies pressure to the reaction medium. The housing is then opened and the removable medium for containing and transferring a test sample is removed from the housing. The housing is closed a second time to a second closed position such that the means for transferring an analyte-indicating agent is in transferable contact with and applies pressure to the reaction medium.

In another embodiment of the invention, various segregated areas of the reaction medium include a specific member of an immunological pair (MIP) which bind to or capture a specific analyte, such as a drug or drug metabolite. Different segregated areas may contain MIPs that are specific for different designated analytes, thereby allowing determinations for more than one analyte to be carried out in a single assay.

The methods and devices according to the invention are particularly beneficial in that only a small amount of signal-producing agent is required, in contrast to the conventional flow through cassettes or devices; applying pressure while maintaining direct contact on the surface of the test device maintains a localized concentration of reagents, particularly the signal-producing agent, which appears to increase the speed and sensitivity of the reaction, e.g., test results are obtained in a matter of seconds versus a matter of minutes or longer; and, in some embodiments, labeling a secondary antibody (as opposed to labeling the primary antibody or the antigen) decreases the reaction time of the assay because the antigen's shape is not altered by being bonded to a label.

DEFINITIONS

1. LIGAND-RECEPTOR ASSAY: any technique involving the detection of the complex formed between a ligand and a substance which binds to the ligand. Preferably, one member of the complex is an analyte. The preferred ligand-receptor assay is an immunoassay. Ligand-receptor assays may be used to determine the presence, absence, quantity, and concentration of ligands in biological fluids. Ligand-receptor assays may be competitive or non-competitive, homogeneous or heterogeneous, direct or indirect, or a combined detection technique, e.g., binding an antibody to a small chemical moiety such as biotin or dinitrophenol (DNP).

It is preferred that during the assay process, substantially all of at least one predetermined ligand or ligand receptor remains in a predetermined position. Any technique for immobilizing a ligand or ligand receptor is included in the scope of the present invention. In a preferred embodiment, a ligand or ligand receptor is bound or immobilized on or in a solid phase. Typical immobilization mechanisms include, but are not limited to, covalent binding, noncovalent binding, chemical coupling, physical entrapment, and adsorption.

2. LIGAND: refers to the analyte itself, or a substance which can be used to infer the presence of an analyte in a test sample. A ligand-receptor refers to the substances for which there is a specific binding partner, e.g., the ligand. As used herein, ligand and ligand-receptors may be members of an immunological pair (MIP). Ligands and ligand-receptors may include haptens, hormones, antigens, antibodies (including anti-antibodies and antibody fragments such as Fab or Fc), DNA, RNA, oligonucleotides, nucleic acids, and complexes or metabolites of any of the above. The ligand or the ligand-receptor may be labeled or unlabeled.

3. ANALYTE: the substance to be assayed, and, depending on the specific assay used, may be a ligand or a ligand-receptor. Exemplary analytes include but are not limited to drugs, proteins, haptens, hormones, metabolites of the aforementioned, and other molecules, alone or in combination with a protein. A hapten is a small molecular weight material, such as some drugs or drug metabolites, which typically first attach to a protein in order to be antigenic or immunogenic. For example, some drugs may be found in the body in both free and bound forms, which in turn provides the ability to distinguish between chronic drug abusers and acute drug abusers. In the case of the former, in many instances an antibody is formed in the body against the bound form which can also be detected as an analyte by the present invention.

4. BIOLOGICAL FLUID: any body fluid which may be tested to determine the presence or absence of an analyte, including, but not limited to blood or a blood component, saliva, urine.

5. Signal-producing AGENT: any agent used in a ligand-receptor assay which can be used to produce a detectable signal. The preferred signal-producing agents provide an easily visible signal, and more preferably a color.

DETAILED DESCRIPTION OF THE INVENTION

Figure 1:
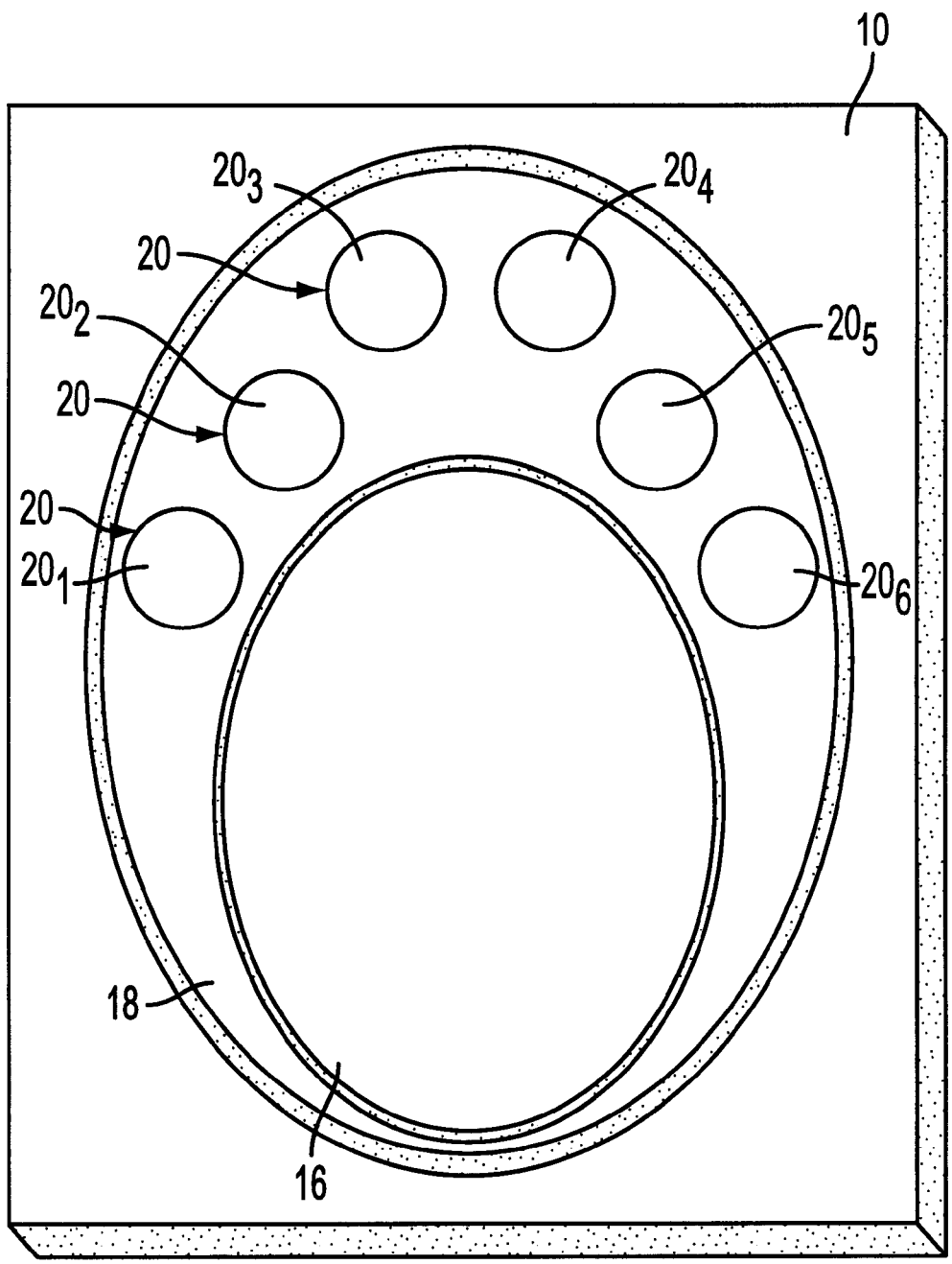
FIG. 1 is a plan view of an assay device according to the present invention.

A ligand receptor assay device according to the present invention includes a reaction medium having at least one reaction zone and, preferably, at least one control zone which is capable of establishing the identity of a test subject. In a preferred embodiment of the invention, the reaction zone includes at least one member of a ligand, ligand-receptor pair (also referred to herein as a "ligand/receptor pair"), this member being capable of establishing the presence or absence of a substance in a test sample. In another preferred embodiment of the invention, the identity of the test subject is established by incorporating a ligand in at least one control zone to provide for a test subject identifying pattern.

A method in accordance with the invention includes conducting, on or in a portion of a reaction medium, an immunological assay for the presence or absence of an analyte in a test sample, and separately establishing the identity of the test subject who provided the test sample on a portion of the reaction medium.

One embodiment of the invention is directed to an assay device, preferably an immunoassay device, comprising a porous support and a reaction medium covering a portion of the porous support. The reaction medium includes at least one reaction zone and, preferably, at least one control zone, wherein the control zone is capable of providing a pattern suitable for identifying a test subject. In a more preferred embodiment, the control zone is capable of providing a pattern comprising a fingerprint or surface reproduction of another part of a test subject's body which can be used for identification. The reaction zone includes a means for conducting a ligand/anti-ligand or ligand/ligand-receptor assay, preferably a means for conducting an assay for the presence or absence of an analyte. In another preferred embodiment, the means for conducting an assay includes a member of an immunological pair.

Another embodiment of the invention is directed to an assay device comprising a reaction medium having at least one reaction zone and, preferably, at least one control zone including a member of an immunological pair, wherein the control zone is capable of establishing the identity of a test subject. The control zone is preferably capable of providing a pattern comprising a fingerprint or surface reproduction of another part of the test subject's body which can be used for identification.

According to another aspect, the present invention includes a support, preferably a porous support; a reaction medium, which is preferably a porous medium, mounted on the support, wherein the reaction medium has at least one reaction zone and preferably at least one control zone, and wherein at least a portion of the control zone is capable of establishing the identity of the test subject. A preferred embodiment includes a member of an immunological pair positioned in or on the reaction medium. In another preferred embodiment, at least a portion of a control zone includes one member of an immunological pair. In some embodiments of the invention, the reaction medium may be unsupported.

The present invention is also directed to a method for processing a sample comprising contacting a reaction zone of an assay device with a test sample; determining the presence or absence of at least one analyte in the test sample; and forming a test subject-identifying pattern in a control zone of the assay device.

The present invention is also directed to a method for determining the presence or absence of an analyte in a sample including conducting an immunoassay for the analyte in a reaction zone of an immunoassay device, whereby the presence or absence of an analyte in a test sample is determined; and establishing the identity of the person providing the test sample in a control zone on the immunoassay device.

A method according to the invention includes determining the presence or absence of an analyte in a sample, preferably by using any ligand binding based assay, and establishing the identity of the person who provided the sample, preferably by using any immunologically based protocol. Referring to FIG. 1, the presence and/or absence of an analyte in a sample may be determined by applying a biological fluid to at least one reaction zone referred to generically as 20, and allowing a predetermined ligand/receptor binding reaction to take place. In a preferred embodiment of the invention, completion of the reaction will result in the production of a signal. Preferably, the signal is produced in the form of a visible color or the absence of color. For example, in FIG. 2, the production of visible color hatched areas $20_1$–$20_3$ indicates the absence of the analyte in the test sample, and the absence of color areas $20_4$–$20_6$ indicates the presence of the analyte in the test sample. It is intended that the invention should not be limited by the specific binding assay employed, the method of producing the signal, the type of signal produced, and the particular location of positive and/or negative results.

Figure 2:
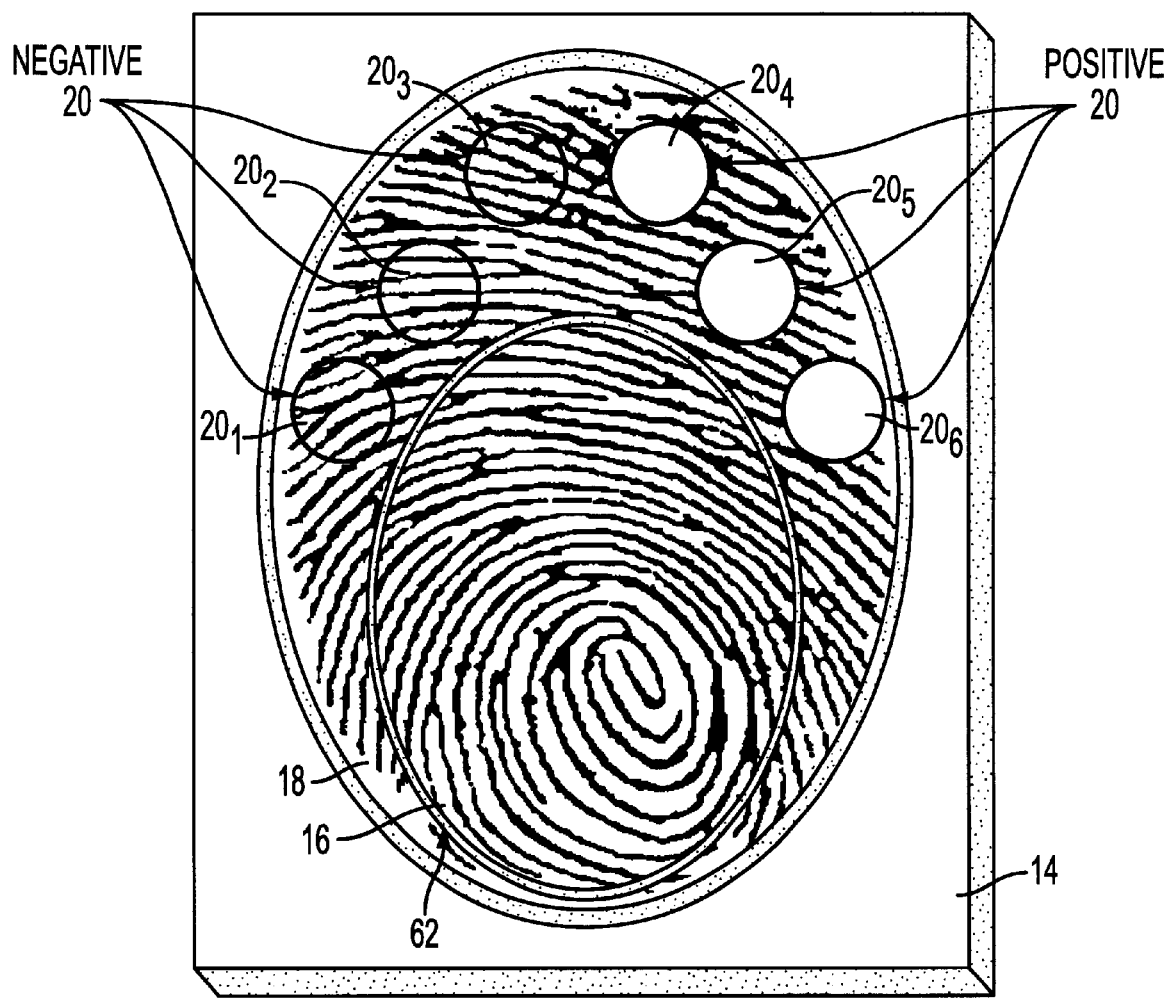
FIG. 2 is a plan view of an assay device according to the present invention, illustrating the results of conducting a test for the presence or absence of an antigen and the formation of a pattern suitable for identifying a test subject.

In accordance with the invention, the production of an image or pattern which identifies the person providing the test sample may be accomplished by applying an identifying body part, such as a person's finger or foot, to a control zone, and allowing a predetermined ligand/receptor reaction to take place, thereby producing the image of a fingerprint or footprint. In a preferred embodiment of the invention, the tip of a person's finger, coated with a signal-producing agent, preferably a color forming agent, is applied to the surface of a control zone having a MIP which will bond to the signal-producing agent coated on the person's finger. In a preferred embodiment of the invention, completion of the immunological reaction will result in the production of a visible color image which corresponds to the person's fingerprint. FIG. 2 shows an exemplary visible fingerprint.

In an embodiment of the invention, particularly for pediatric use, the image or pattern which may be formed may be of the foot or a portion of the foot. In this embodiment, the foot or a portion of the foot, previously coated with a labeling reagent, may be applied to an apparatus according to the invention.

Exemplary embodiments of the invention will now be described by reference to the figures.

An immunoassay device 10 according to the invention includes a reaction medium 14, preferably mounted on a support or base member 12. Base member 12 is preferably a porous support. In a preferred embodiment of the invention, the reaction medium 14 includes at least one reaction zone 20 and at least one control zone 16. In the exemplary embodiments shown in FIGS. 1 and 2, the immunoassay device 10 includes six reaction zones 20 (numbered $20_1$–$20_6$) and two control zones 16 and 18.

In a detection apparatus, 10 according to the invention, at least one of the reaction zones, 20 include means for conducting an immunological assay, preferably to establish the presence and/or absence of an analyte in a test sample. In the exemplary embodiment shown in FIG. 3, reaction zones, 20 include at least one carrier, such as particles 22, embedded in reaction medium 14. As shown, the particles 22 are coated with a member of an immunological pair 21.

In a detection apparatus 10 according to the invention, at least one of the control zones 16 include means for establishing the identity of a test subject, preferably including a member of an immunological pair. In the exemplary embodiment shown in FIG. 4, control zone 16 includes a carrier, such as particles 24, embedded in the reaction medium 14. As shown, the particles 24 are coated with a member of an immunological pair 25. In a preferred embodiment of the invention, the MIP 25 is capable of bonding to a signal-producing agent, or to a MIP-signal-producing agent conjugate.

Figure 5:
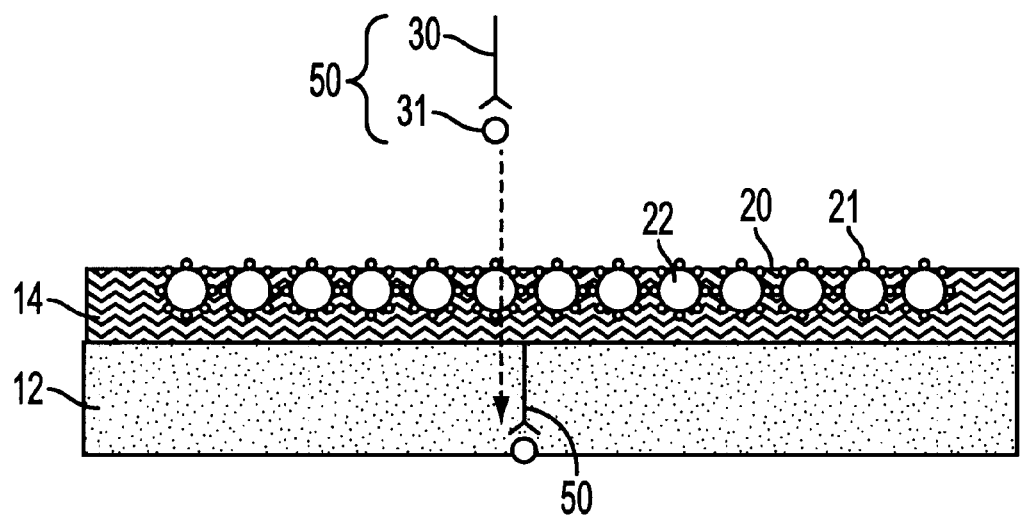
FIG. 5 is an enlarged schematic cross sectional view of an assay device according to the present invention, illustrating a positive test result.

An exemplary method according to the invention may be described by reference to FIGS. 5–8. In FIG. 5, the presence of an analyte 31 in a test sample to which a MIP 30 has been added can be determined. The biological fluid is applied to the surface of a reaction zone 20 having particles 22 coated with a member of an immunological pair 21. If analyte 31 is present in the biological fluid, it will bond to or be captured by MIP 30, with which it is mixed and incubated and which is specific for analyte 31. The resulting immunological pair 50 will not bond to or be captured by MIP 21, and will pass through the reaction medium 14. According to this embodiment of the invention and in this situation, no color forming agent will bond to the coated particles 22.

Figure 6:
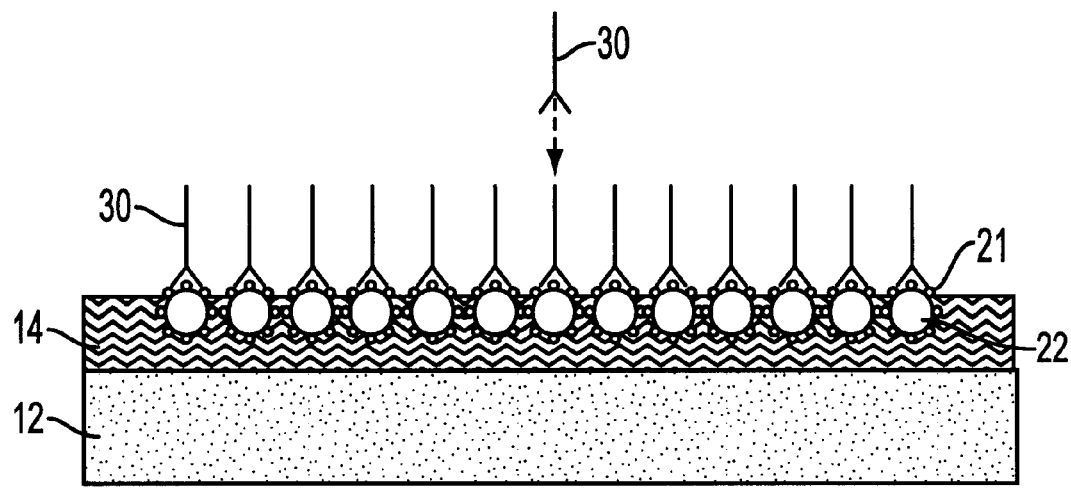
FIG. 6 is an enlarged schematic cross sectional view of an assay device according to the present invention, illustrating a negative test result.

In FIG. 6, the absence of an analyte in a test sample to which a MIP 30 has been added can be determined. The biological fluid is applied to the surface of a reaction zone 20 having particles 22 coated with a member of an immunological pair 21. In the absence of analyte in the biological fluid, MIP 30 will bind or be captured by MIP 21. According to this embodiment of the invention and in this situation, a color forming agent applied to the surface of the reaction medium will bond to MIPs 30 on the coated particles. In an alternative embodiment of the invention, the MIP 30 may include the color forming agent.

Figure 7:
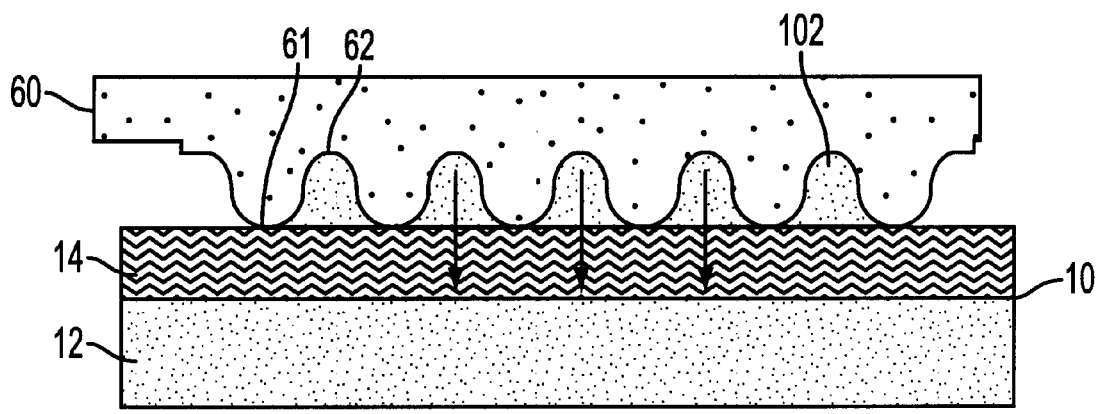
FIG. 7 is an abstract representation of a cross section of an assay device according to the present invention, illustrating contacting the assay device method according to the invention.
Figure 8:
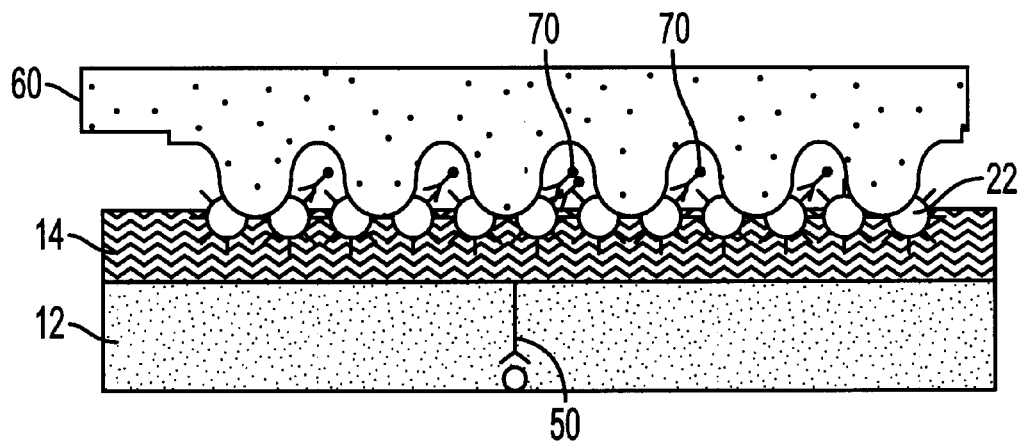
FIG. 8 is an abstract representation of a cross section of an immunoassay device according to the present invention, illustrating the formation of a fingerprint in a control zone of the reaction medium.

FIGS. 7 and 8 illustrate an exemplary method of producing the image of a fingerprint on the surface of a control zone. The surface 60 of a person's finger includes ridges 61 and valleys 62. When a person's finger is coated with a color forming reagent 102, a greater portion of the color forming reagent will tend to collect in the valleys 62. When the finger is applied to the surface of the reaction medium 14, it is believed that zones of higher concentration color forming reagent localize in the area of the valleys. The coated particles in the surface of the control zone will typically bond to a higher proportion of the color forming reagent, which will in turn produce a more intense visible color corresponding to the valley of the person's fingerprint.

In a preferred embodiment of the invention, determining the presence/absence of a substance in a biological fluid and producing the image of a fingerprint are typically accomplished in only a few minutes.

Both the rapidity and higher sensitivity of the test devices and method of the present invention are attributable to characteristics of both the device and manner of applying reagents and/or test sample to the membrane surface and, to some extent, the materials from which the membrane is formed. Thus, as described below, the manner of application and materials are such that reagents in solution are maintained in contact with the membrane surface for a longer period of time to promote a greater degree of reaction between reagents in the membrane surface and reagents in solution. This leads to higher sensitivity and requires smaller concentrations of reagents.

Individual aspects of the invention will now be described in greater detail.

Ligand-Receptor Assay

In accordance with the invention, the detection device may be used with any assay technique for detecting an analyte of interest. In all of the assays used in accordance with the present invention, an analyte is bound to at least one ligand or ligand-receptor. Exemplary binding assays include but are not limited to labeled ligand assays, including competitive binding assays in which a solid phase is coupled to the binding reagent, such as simultaneous or sequential incubation with one or more separation steps, and displacement assays; and labeled binding reagent assays, including noncompetitive and competitive binding assays, including assays in which the solid phase is the binding reagent or the ligand, and sandwich assays, including precipitation, radioimmunoassay, or enzyme-linked immunosorbent assay. It is intended that the invention is not to be limited by the type of immunoassay employed or the specific protocol used in performing the assay. Exemplary immunoassays techniques are shown in the Examples.

Reation Medium

In accordance with the invention, the reaction medium may be any medium suitable for performing a ligand-receptor assay. As noted above, the reaction medium includes at least one reaction zone to indicate the presence or absence of an analyte and, preferably, at least one control zone to indicate the identity of the test subject. Typically, ligand-receptor assays may be conducted using a reaction medium in the form of beads, tubes, plates, paddles, a porous or non-porous matrix, or porous or non-porous membranes or filters.

The reaction medium can include a depth medium wherein the surface or an area near the surface comprises at least one reaction zone. The reaction medium may also include a layered structure having a reaction zone as a surface layer. In accordance with the invention, the reaction and control zones are positioned in the reaction medium so that a signal-producing agent, if present, can be readily visualized.

In accordance with the invention, the preferred reaction medium is porous, and even more preferred, a porous membrane. It is intended that the invention should not be limited by the type or construction of the reaction medium. One skilled in the art will readily recognize that the choice of reaction medium depends on the desired physical properties, including, but not limited to properties such as sensitivity, binding capacity, stability, the type of molecules or MIPs which can be bound, and compatibility with a particular assay protocol.

Exemplary materials for forming the reaction medium include, but are not limited to latex, nitrocellulose, nylon, cellulose, and nylon.

A preferred reaction medium is the commercially available Gelman Supor membrane. Supor membrane is a latex low protein binding polysulfone membrane with a hydrophilic surface. One skilled in the art will recognize that this membrane may be desirable because it provides superior flow rate and particle retention; a smooth surface; brilliant whiteness and opaqueness to enhance signal contrast in diagnostic tests; low extractables to reduce sample contamination and background interference; and uniform porosity to ensure final product consistency. Also, the use of this membrane obviates the need for an external wetting agent, which may be desirable for controlling the introduction of unwanted extractables.

Another preferred membrane, IAM, Immobilon Affinity Membrane (commercially available from Millipore corporation; see, for example, U.S. Pat. No. 4,407,943), the hydrophobic base polymer, polyvinylidenedifluoride (PVDF), binds proteins. IAM also permits a high degree of control over the extent of protein binding and the user can reproducibly immobilize nanogram to microgram quantities of protein on the surface to suit various assay requirements. Binding a ligand to IAM and its use in immunoassays is known in the art.

The use of membranes, as the solid support in a reaction medium of the present invention may be desirable for the added convenience of a solid phase, the typically high protein binding capacity, and the membrane's flow-through characteristics. Nitrocellulose is one of the most commonly used membranes due to its high affinity for proteins nucleic acids, other cellular antigens, and cellular macromolecules, and may be desirable if the desired MIP binding is ionic or hydrophobic. Nitrocellulose also provides an excellent matrix for blotting proteins and nucleic acids. The nitrocellulose may be cut into whatever shape is required and has the useful characteristic that the amount of protein in a fingerprint will be clearly visible.

Included within the scope of the present invention is changing or incorporating different surface properties on the membrane in order to achieve a desired result, e.g., the surface properties of a membrane designed for a competitive binding assay for a hormone may be different than an immunometric assay for a therapeutic drug. For example, it has been shown that treating the surface of a hydrophilized PVDF membrane with ethanolamine reduces the non-specific binding of the membrane surface. Selection of a particular surface treatment agent or surface property may be based on the desired chemical characteristic to be imparted to the surface; the inability or reduced capability of denaturing or impairing the functionality of a bioactive agent on or in the reaction zone; the desire to effect a certain orientation of an immobilized bioactive molecule; the desire to promote long-term stability of an immobilized bioactive molecule; the inclusion of a desired nucleophilic substituent; and the availability and cost of treatment agents. The use of other surface treatment agents, including bifunctional or multifunctional reagents, to affect the surface properties of the membrane are included within the present invention.

One skilled in the art will readily recognize the benefit derived by including a reaction medium which is porous. Positive test samples will readily pass through the reaction medium, obviating the need to wash the surface of the reaction medium prior to adding a color-forming agent. Although it is less desirable, it is intended that the invention include the use of a non-porous medium. A preferred support material is a somewhat rigid porous plastic material known as Porex.

As noted above, the reaction medium may be supported or unsupported. In the preferred embodiment, the reaction medium is supported, and even more preferred, the support is porous. An exemplary support includes, but is not limited to polystyrene.

In another embodiment of the invention, the support may be impermeable to the fluids and reagents used in conducting the testing; in this embodiment, the reaction medium is preferably "deep" enough to have a reaction zone at or near the surface of the medium.

In preferred embodiments of the present invention in which the device is totally or substantially self-contained, that is, needing no additional reagents or with at most a few drops of a buffer solution or water to rinse the reaction medium, and needing only a minimum level of skill to perform an accurate determination, another type of material is preferred to support the reaction medium. For such applications, a compressible wicking or sponge-like material is preferred. Thus, by applying pressure to the outer, substantially planar surface of the reaction medium, which is adjacent, in contact with or bonded to a substantially planar surface of the compressible support material, causes compression of or an indentation in the surface of the support material adjacent the reaction medium, such that the support surface is caused to be below its uncompressed planar surface. In the presence of a liquid, after pressure is released from the compressible support material and as the compressible material expands to its uncompressed state, the liquid is drawn into the support material. Thus, if a liquid sample, reagent solution, buffer solution or water is applied to the reaction medium and sufficient pressure is applied to cause a deformation in the surface of the support material, liquid will be pulled into the support material as it expands to its original state. The pressure applied is a function of the compressibility of the material. A preferred compressible support material is a compressible, flexible reticulated urethane foam, preferably a polyester or polyether urethane foam having a pore rating of about 75 to 100 ppi, preferably about 80 to 90 ppi. Such materials are available from E. M. Murray Co. Inc.

Control Zone

In a preferred embodiment of the invention, the reaction medium includes a control zone for establishing a reference point in determining the presence or absence of an analyte in a test sample (reference control zone), and most importantly a control zone for establishing the identity of the test subject who provided the test sample (identity control zone).

In accordance with the invention, a control zone for establishing the identity of the test subject (identity control zone) who provided the test sample may include any signaling mechanism which incorporates a MIP. For example, the control zone may include a member of an immunological pair capable of bonding to a signal-producing agent, which when applied by contacting the test subject's finger to the surface of the identity control zone, an image of the fingerprint is produced on the test device.

As used herein, "capable of establishing the identity of a test subject" refers to the capability of specifically identifying the subject who provided the sample being tested. In a preferred embodiment of the invention, the control zone includes a member of an immunological pair which, when placed in contact with the test subject's finger which has been previously coated with a signal-producing agent, is capable of producing a permanent image of a fingerprint, preferably a fingerprint image easily visible. In another embodiment, the invention includes a control zone having a member of an immunological pair or nucleotide sequences which are capable of bonding to nucleotide sequences which can be used to identify the test subject.

In accordance with the invention, the control zone for establishing a reference point in determining the presence or absence of an analyte in a test sample includes any means for providing a control. Several examples for providing a control are shown in the examples. It is intended that the invention not be construed as being limited by the means or mechanism for establishing the standard of comparison in judging the test results.

Reaction Zone

The reaction zone refers to the locus in which the presence or absence of an analyte can be determined. For example, the reaction zone is preferably on or near the surface of the reaction medium, or may be below the surface. In a preferred embodiment of the invention, the reaction zone includes at least one ligand or ligand-receptor bound to a particle or bead in a matrix or filter, suitable for capturing an analyte of interest. In another embodiment of the invention, at least one of the reaction zones may be a control for establishing a reference point, e.g., a comparative control to show the absence of color.

Signal-producing Agent

A signal-producing agent refers to any agent or marker which produces a detectable signal or which permits the detection of a ligand or ligand-receptor. Preferred signal-producing agents are those which permit detection of the analyte without instruments, preferably by visual means. Exemplary signal-producing agents include, but are not limited to color forming agents, such as an enzyme, polymer containing dyes, chemiluminescent agents, fluorescent agents, radioisotopes or ferromagnetic particles. The color forming agent may be a colored particle, a colored molecule or some species, such as an enzyme, which is capable of triggering a sequence of events leading to the formation of a colored marker. The colored molecule may be a fluorescent dye, such as fluorescein or rhodamine; a chemiluminescent compound; a bioluminescent compound; or a compound that may be detected by the absorption of electromagnetic radiation (and possible reemission of radiation at another wavelength), including ultraviolet radiation, visible radiation and infrared radiation. The colored molecule may be directly or indirectly conjugated to a ligand or ligand-receptor. Alternatively, the colored molecule may be incorporated in a particle, particularly a microsome.

Enzymes, useful as color forming agents, include alkaline phosphatase, horseradish peroxidase or B-galactosidase. Such enzymes are often used in conjunction with a chromogenic substrate. A list of some exemplary chromogenic substrates which may be used with enzyme color forming agents are given below in Example 11.

In a preferred embodiment of the invention the color forming agent may be an electron dense particle, such as colloidal gold, silver coated colloidal gold or ferritin.

In another preferred embodiment of the invention, the color forming agent is capable of bonding to a MIP.

The present invention includes a signal-producing agent, which may be a color forming agent. Preferably, the signal-producing agent comprises a labeled MIP, for detecting the adsorption of an analyte or an analyte conjugate in or on the reaction medium. The labeled MIP may comprise any one of a number of appropriate labels, such as an enzyme, a fluorescent compound, a bioluminescent compound, a ferromagnetic atom or a colored particle or microsome. In a preferred embodiment, the label used in the present invention is colloidal gold. Gold is biologically inert, has very good charge distribution and is widely available in many useful forms. Its detection can be enhanced using several silver deposition methods, which permit development to be monitored by the naked eye. Colloidal gold particles conjugated with a wide range of anti-immunoglobulin antibodies, protein A or streptavidin are available commercially.

While a colloidal gold substrate is preferred over other dyed particles or microsomes, a chromogenic substrate provides an alternate sensitive detection method for the enzyme conjugate.

Figure 11:
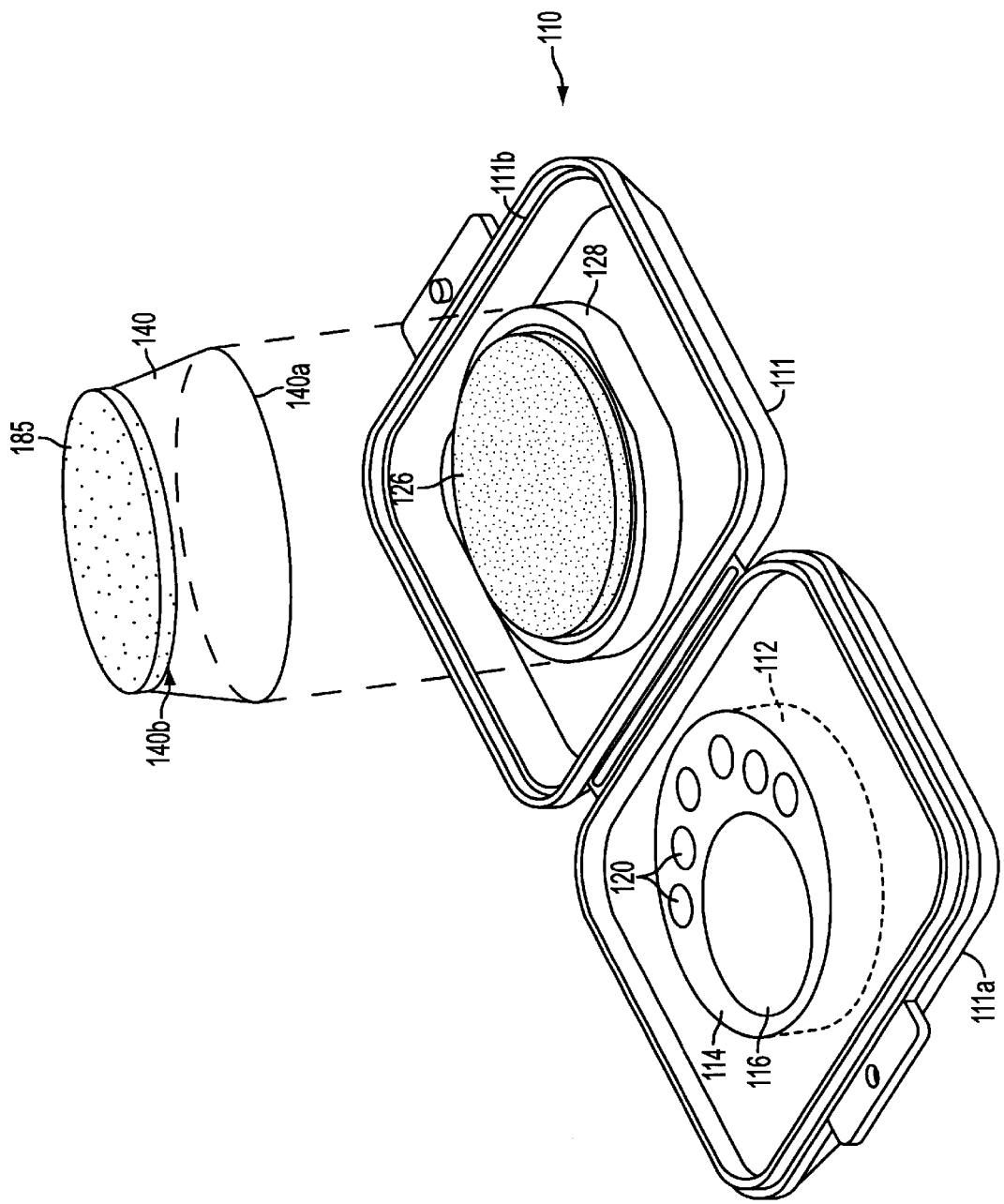
FIG. 11 is an open, exploded perspective view of one embodiment of a device according to the present invention.

Several embodiments of the present invention relate to compact assay devices and kits which contain all or most of the reagents and materials necessary for qualitative and/or quantitative determinations of one or more analytes. A preferred embodiment of such a device is illustrated in FIG. 11 which shows a self-contained assay device 110. The device includes a housing 111 which in a preferred embodiment includes a first part 111a and a second part 111b. Located within the first part of the housing 111a, mounted on the upper surface of a raised plateau or platform portion of a base member 112 is a reaction medium 114, of the type described above. The base member 112 preferably includes a porous support adjacent, in contact with or bonded to the reaction medium 114. In a preferred embodiment of the invention, the reaction medium 114 includes one or more reaction zones 120, each of which includes a specific reagent, such as a member of a ligand/receptor pair (which may be a member of an immunological pair, for example an antigen or an antibody). The reaction medium in this preferred embodiment also includes at least one control zone 116. As in the embodiments discussed above, each of the reaction zones includes a reagent suitable for determining the qualitative presence or the quantitative range of an analyte. In a preferred embodiment of the invention, a control zone is suitable for identifying the donor of a test sample. Likewise, the control zone 116 also includes a suitable test reagent for identifying the test subject which is preferably a member of a ligand/receptor pair, such as a member of an immunological pair.

The reagents present in each of the reaction zones may be applied manually or, preferably, using an automated process, such as using an ink jet sprayer of the type used in ink jet printing systems, to apply the reagent in individual and segregated reaction zones.

In the second part of the housing 111b, is located a medium 126 on which is spread at least one signal-producing agent, or analyte-indicating agent, which is preferably a color forming agent. The signal-producing agent-containing medium 126 is formed from a material which is of a lower porosity than either the reaction medium or the medium for containing a test sample (discussed below). Preferable for use as the medium on which the signal-producing agent is spread is a closed cell polyolefin material, such as a closed cell polyethylene or polypropylene. A preferred material is available as Minicell from Voltek Corporation. The signal-producing agent, as with the other embodiments of the present invention, preferably is a labelled member of a ligand/receptor pair, such as a labelled member of an immunological pair, such as a colloidal gold labelled substance. The medium 126, containing the signal-producing agent, is positioned in the second part of the housing 111b in such a way that when the two parts of housing are brought together in a specific closed position, contact is made between the medium 126 and the reaction medium 116 such that signal-producing material contained in the medium 126 is transferred to the reaction medium. This is preferably accomplished by mounting the medium 126 on a base portion 128 which resembles an elevated plateau or platform, which in the preferred embodiment shown in FIG. 11 has a shape similar to base 112. This arrangement, in which the medium containing the signal-producing agent is spaced apart from the reaction medium 114 in a first or open position and transfers the signal-producing agent to the reaction medium 114 in a second or specific closed position, apparently achieves greater sensitivity and increased speed due to the pressure applied when the signal-producing agent-containing medium 126 contacts the reagent medium 114. Depending upon the specific materials involved, a pressure in excess of atmospheric may be used, preferably slightly less than about 2 to about 5 psi, for a period of about 5 to about 20 seconds is sufficient to adequately retain the signal-producing agent at or near the surface of the reaction medium after the media 114 and 126 are placed in contact with one another. Although higher pressures can generally be used to transfer either the signal-producing agent, analyte or conjugate formed of the analyte with a ligand receptor of the analyte (as discussed below), the duration of time for exerting the pressure is decreased, since pressure and time vary inversely.

Another component of the self-contained or "integrated" device illustrated in FIG. 11 is a medium 185 for containing and transferring a portion of a test sample to the reaction medium 114. The medium 185 used to hold both a test sample and a reagent capable of reacting with an analyte is a hydrophilic material, preferably in the form of a hydrophilic sponge and preferably is formed from a fine pored polyester urethane sponge material. A preferred material is polyester urethane foam sponge material having a porosity of 100 ppi that is available from E. N. Murray Company Inc. The medium 185 serves several purposes. First, it is capable of absorbing a test sample taken from a donor or test subject. It is also capable of transferring the sample or a conjugate formed from an analyte present in the test sample and a receptor against the analyte to the reaction medium 114. The medium 185 is also capable of providing diffusion and reaction loci for both the substances present in the test sample, as well as a reagent present in the medium. This reagent is preferably a member of a ligand/receptor pair, such as a member of an immunological pair of the type discussed above and identified in FIGS. 5 and 6 as MIP 30. The reagent in the medium 185 is typically an antibody. This reagent is contained in the medium 185 preferably as a lyophilized antibody. In this embodiment, the sponge medium 185 is treated with a solution of reagent and the treated sponge is subjected to a lyophilization treatment in a lyophilization chamber, such as a Speed-Vac.

The medium for containing the test sample and the test sample and the reagent, preferably in lyophilized form, may be mounted at one end of a removable cylindrical member 140. In the embodiment illustrated in FIG. 11, the open end 140a opposite to the closed end 140b of the cylindrical member 140 on which the medium 185 is mounted, is larger in shape or diameter than the base portion 128 of the housing part 111b on which the signal-producing agent-containing medium 126 is mounted. Preferably the open end 140a of the cylindrical member 140 is commensurate in shape to the base portion 128 so that the cylindrical member 140 may be easily accommodated in the housing part 111b over the base portion 128. The cylindrical member 140 is of such a shape and configuration that in an "open" position of the housing parts in which the media 114 and 126 are in spaced-apart relationship with one another, the medium 185 is also in spaced-apart relationship with both of the media 114 and 126 in the open or first position of the housing members 111a and 111b. In a second or specific "closed" position of the housing members 111a and 111b, while remaining within the housing 111 and in spaced relationship to the base 128 and signal-producing agent-containing medium 126, the medium 185 for containing the sample contacts and transfers substances present in the sample and/or a ligand/receptor pair formed between an analyte found in the sample and a conjugate thereof to the reaction medium 114. Thus, in the second or closed position, pressure is exerted by the end 140b of the cylindrical member and medium 185 on the reaction medium 114 in much the same manner as in the contact which occurs between the medium 126 containing the signal-producing agent and the reaction medium in a second closed position. The method of using this device is discussed below.

While FIG. 11 illustrates an embodiment of the present invention which employs a two-part housing 111 having a first part 111a and a second part 111b, and a removable cylindrical member 140 on which a sponge 185 for containing a test sample is attached, other aspects and alternative embodiments are contemplated by the present invention. For example, the housing parts 111a and 111b are illustrated in FIG. 11 as being joined to each other by a flexible hinge arrangement. When the housing is formed from a suitable plastic, which is preferably substantially inert to any of the reagents or materials used in other components of the device or in solutions applied to the media of the device, the hinge may be formed from a thinner portion of the same plastic material. Thus, the housing may be formed as a single unit in one pressing operation. Alternatively, another material may be used as the hinge material and the hinge attached to the housing parts by suitable means.

In another embodiment, the housing parts 111a and 111b need not be joined to one another at all. Thus, to close the device, the separate parts may be constructed to snap into place with a detent or some similar arrangement or may engage one another with a threaded arrangement or a bayonet engaging arrangement.

In yet another alternate embodiment, the medium 185 for containing the sample and containing a test reagent, rather than being mounted on the removable, cylindrical member 140 of the type shown in FIG. 11, may be located in a third housing part. When used with housing parts which are permanently joined to one another, such as that described immediately above, the housing part containing the sponge for containing a test sample may be placed intermediate the separate housing parts containing the reaction medium and the signal-producing agent-containing medium (equivalent to housing parts 111a and 111b). In this instance, however, the intermediate housing part containing the sponge 185 may engage one or both of the other housing parts and contact the reaction medium in the first housing part when in place and forming part of the housing. It may also be removed when it is desired to contact the reaction medium 114 with the medium containing a signal-producing agent 126.

In yet another embodiment, the housing part containing the hydrophilic sponge for containing a test sample may be joined to the first housing part (equivalent to housing part 111a as shown in FIG. 11) by means of a hinge on the edge portion of the first housing part in opposing relationship to the edge of the first housing part to which the second housing part is joined. Thus, when it is desired to place the sponge containing a test sample in contact with the reaction medium, the third housing part containing the sponge may be rotated to a substance-transferring position in contact with the reaction medium and thereafter rotated to a spaced apart position with respect to the reaction medium and the second part of the housing containing the signal-producing agent medium 126 may be rotated into transferable contact with the reaction medium.

The above embodiments of the present invention which include three media (a reaction medium, a medium for containing a test sample, and a medium containing a signal-producing agent) are substantially self-contained. Thus, it is unnecessary to add additional reagents in order to perform the assay. At most, a buffer solution, such as a phosphate buffered solution, or water may be used in a final step to rinse the reaction medium to remove residual reagents from the surface of the reagent medium. Alternatively, when a compressible porous medium is used as a support for the reaction medium, it may be unnecessary to use any supplemental materials.

Figure 12:
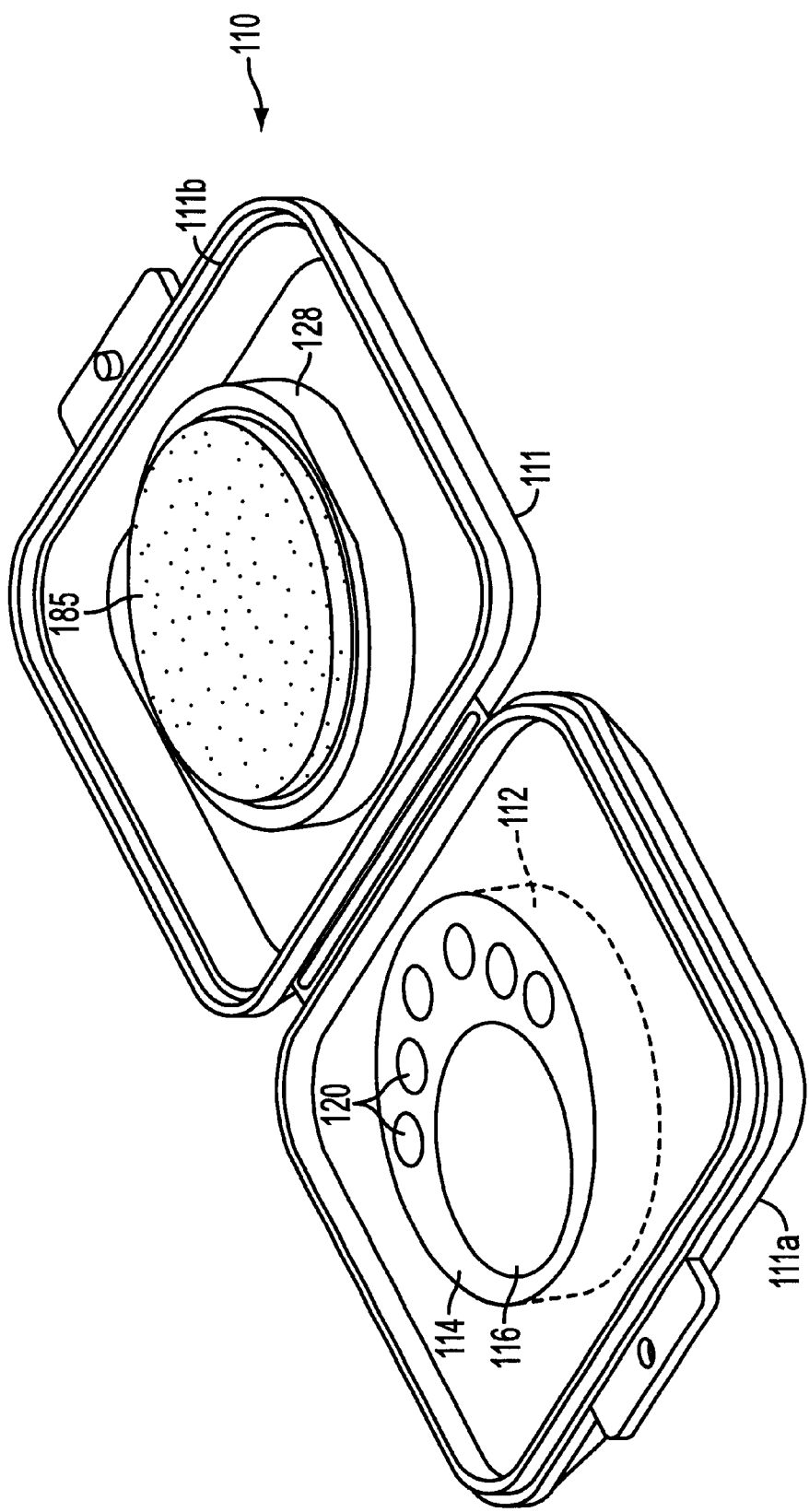
FIG. 12 is a perspective view of another embodiment of a device according to the present invention.

The present invention also contemplates compact assay devices using only two media, rather than the three-media devices discussed above. Thus, in the embodiment illustrated in FIG. 12, while still retaining the reaction medium 114 mounted on base 112 in a first part of the housing, the sample-containing and transferring sponge 185 may be mounted directly on the base 128 instead of the signal-producing agent-containing medium 126 being located thereat. In such an embodiment, the removable cylindrial member 140 on which the medium 185 is mounted in the "3-media" embodiment illustrated in FIG. 11 may be dispensed with. In such an embodiment, the wash bottle containing a buffer, detergent or water may be used in the same manner as described above. However, in this embodiment, the signal-producing agent may be dispensed from a reagent bottle directly on the finger or other identifying body part of the test subject and the finger or other body part may be placed in contact with the reaction medium after the test sample has been placed on the sponge 185 mounted in base 128, incubation has taken place and the housing has been closed such that there is substance transferable contact with suitable pressure between the surface of sponge 185 and the reaction medium 114.

Figure 13:
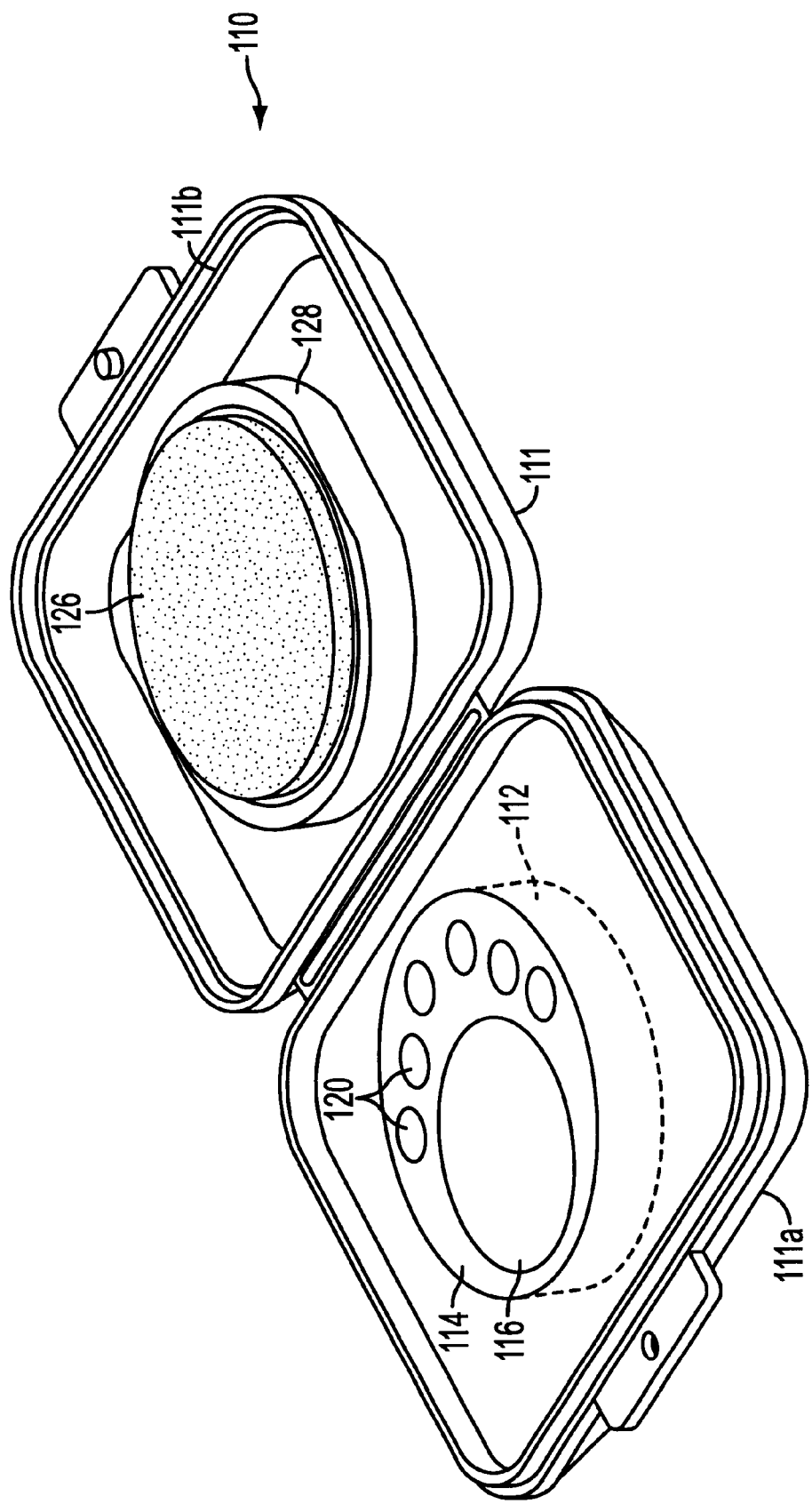
FIG. 13 is a perspective view of still another embodiment of a device according to the present invention.

Another two-media device is illustrated in FIG. 13. Like the embodiment discussed above and shown in FIG. 11, this includes the reaction medium 114 mounted on base 112 in a first part of the housing and the signal-producing agent-containing medium 126 in the second part of the housing. This corresponds substantially to the embodiment shown in FIG. 11 without the removable cylindrical member 140 and medium 185 for containing a test sample. This embodiment, like the 3-media device illustrated in FIG. 11 does not require the presence of the test subject, and, accordingly, will not produce a fingerprint or other identifying mark of the test subject when the test subject is not present. Alternatively, however, a fingerprint can be produced when the test subject is available at the time the test is performed. In this embodiment, the sample is mixed with a test reagent supplied with the device, most suitably in a reagent bottle, as part of a kit. The reagent may include one or more substances capable of indicating the presence of one or more analytes and is preferably a member of a ligand/receptor pair, most preferably a member of an immunological pair capable of forming a conjugate with a specific analyte. The mixture of test sample and reagent is applied dropwise to the surface of the reaction medium, sufficient time for incubation allowed and the housing is closed for a short period of time so that there is contact between the signal-producing agent-containing medium 126 and the reaction medium sufficient to transfer the signal-producing agent to the surface of the reaction medium. If the test subject is present at the time of testing, rather than closing the device to make contact between the media 114 and 126, the test subject may roll a finger on the surface of the signal-producing agent medium 126 and then press the finger on the reaction medium.

Another embodiment of the present invention is directed to a device and method for distinguishing between an acute and a chronic drug abuser. Thus, in the body of one who uses a drug, not only are molecules of the drug or a metabolite found, but the drug or such metabolite binds to a carrier molecule. Continued use of a drug stimulates production of an antibody against the carrier bound drug. Thus, in the body of a human who chronically uses a drug may be found not only a residue of the drug or metabolite thereof, but also the presence of a human antibody to the drug. In an embodiment of the device according to the present invention, a reaction zone in the reaction medium may be spotted with some of the drug of which the test subject is suspected of using. This will then form a conjugate with the human antibody to the drug if present as an analyte in a test sample. As a signal-producing agent for indicating the presence of the drug antibody may be used the corresponding goat or mouse antihuman labelled antibody.

Method of use

An assay method in accordance with the invention includes conducting a ligand-receptor assay for an analyte in a reaction zone of an assay device, whereby the presence or absence of an analyte in the test sample is determined, and establishing the identity of the person providing the test sample in a control zone on the assay device. In a preferred embodiment of the invention, establishing the identity of the person providing the test sample may be accomplished using ligand-receptor assay methods, e.g., binding a MIP to a signal-producing agent.

As noted above, the biological fluid sample to be tested for the presence or absence of at least one analyte is applied to the surface of the immunoassay device according to the invention. Any means of applying the fluid sample to the detection apparatus may be used. For example, in one embodiment of the invention, the biological fluid, e.g., urine, may be combined with a MIP according to standard immunoassay procedures, drawn into a pipette, and deposited on the surface of the test device.

In another example, the biological fluid, e.g., blood, may be collected in a pipette and deposited on the surface of the test device, or may be smeared on a solid applicator, such as a fingertip. In one preferred embodiment, blood is smeared on the test subject's fingertip, which is then pressed in contact with the surface of the detection device. In another preferred embodiment, the biological fluid is combined with a MIP before application to the reaction medium. In still another preferred embodiment, the sample is deposited on the surface of a medium for containing a test sample. Other exemplary methods of applying the test sample to the detection device are shown in the Examples.

A preferred embodiment of the invention includes applying one or more reagents or a sample to a surface of the test device using pressure. For example, it has been found that smearing a signal-producing agent on the test subject's fingertip and applying the fingertip to the test device significantly reduces the amount of signal-producing agent required, and significantly increases the sensitivity and speed at which the assay proceeds. For example, as little as 10 microliters and preferably about 12 microliters of colloidal gold can be smeared on the test subject's fingertip in order to perform the assay. In contrast, as much as 100 microliters or more of the signal-producing agent is typically required for conventional flow-through cassette assay devices. In a like manner, another preferred embodiment includes the use of pressure in the application of sample to the surface of the reaction medium.

While not intending to be limited to a particular theory of operation, it is believed that the pressure and/or surface tension which occurs when the test subject's finger is placed on the assay device results in localizing an increased concentration of ligand and ligand receptor, increasing the amount of time that the reagents are retained in a localized area of the assay device, and may involve migration of the signal-producing agent from the ridges of the fingerprint to the valleys, to produce a clear fingerprint pattern on the surface of the test device.

The higher sensitivity and reduced amounts of reagents provided by the present invention seems to result from a more complete reaction taking place at the surface of the membrane where immobilized reagent is found. The more complete reaction results apparently from the reagents applied to the surface of the membrane in liquid form being maintained thereat for a longer period of time. Thus, as is typical with most known test devices, liquid samples and/or reagents are applied in drop form to the surface of a membrane which contains either reagent or test sample and are quickly drawn through the membrane, either because of an absorbent placed in contact with the membrane on its downstream surface or because of the nature of the membrane material. In the present invention, however, the liquid containing the reagent and/or sample is applied to the surface of the reaction medium and is maintained thereat with the application of pressure greater than atmospheric pressure as a thin film which shows little tendency to pass completely through the membrane. Thus, using the finger as an applicator or another applicator means, such as an applicator means included as part of the device, reagent-containing liquid on the applicator is transferred to and maintained at the upstream surface of the reaction medium under pressure. Thus, while not wishing to be held to any theory, it appears that primarily the surface tension of the liquid, in combination with other factors such as the capillary action of the applicator and possibly the porosity of the medium on which the liquid is placed in combination with the pressure causes a thin film of liquid to be maintained at the upstream surface rather than passing through the medium as long as the pressure is maintained on the outer surface of the medium. The contribution of the surface tension in maintaining a thin film at the surface of the reaction medium appears to increase the availability of the substance(s) present in the liquid to reagents in the medium. Thus, using an applicator, such as the finger, with a pressure greater than atmospheric pressure, typically as little as about 1 to about 5 psi and up to a pressure that a test subject would normally and comfortably apply (such as in pressing the finger in making an "official fingerprint"), prevents the liquid from passing through the membrane until the pressure is removed. Application of pressure would normally be for a period of time of about 5 to 20 seconds. Maintaining the reagent at the surface of the medium or membrane for this period of time is sufficient to assure a greater degree of reaction of the reagents located at or immediately below the upstream surface of the medium. While the nature of the liquid, such as its surface tension, as well as the materials from which the membrane and applicator are formed, have some bearing on this phenomenon, it appears that a variety of materials may be used and the phenomenon of maintaining the thin film of liquid at the surface of the membrane still occurs. Furthermore, and also not wishing to be held to a particular theory, it appears that the increased sensitivity and particularly the rapidity of the assay determinations of the devices and methods of the present invention may be attributed, at least in part to the use of pressure at the time liquid solutions are applied to the surface of the reaction medium. It is believed that the pressure applied, which is greater than atmospheric pressure and is typically as little as 1 psi and preferably in the range of about 2 to 15 psi, increases the kinetics or the speed of the particular reaction taking place.

The test device preferably includes one or more MIPs immobilized in a corresponding number of reaction zones. For example, if the analyte of interest is an antibody, the test device may include an antigen bound to microspheres or particles embedded in the reaction zone. One skilled in the art will recognize that a desired amount of antigen can be immobilized in the reaction zone, and that a threshold concentration of bound MIP may be used to detect a predetermined amount of analyte. In one embodiment of the invention, the detection device includes several reaction zones, each reaction zone for a different analyte, and each reaction zone includes a predetermined threshold concentration of bound MIP to detect a predetermined amount of analyte. As used herein, threshold amount or concentration refers to the lower limit of a concentration range for an analyte. In another embodiment of the invention the detection device includes several reaction zones, each reaction zone including a different threshold concentration for the same analyte. In this embodiment, the threshold concentration provides a reference point for determining the upper limit of an analyte concentration range. As shown in the examples below, varying the threshold concentration in the reaction zones may provide an exemplary method of quantifying the amount of analyte in a sample.

After the biological fluid being tested has been applied to the surface of the detection device, the presence or absence of the analyte in the test sample can be determined, preferably by visually ascertaining a color (signal) or the absence of a color (signal). In a preferred embodiment of the invention, a positive response, i.e., indicating the presence of the analyte in the biological fluid, corresponds to the absence of color. In a preferred embodiment of the invention, a negative response, i.e., indicating the absence of the analyte in the biological fluid, corresponds to a visualized color. However, in one embodiment of the invention in which a determination is made as to whether the test subject is a chronic drug abuser in which a human antibody to a drug is being tested for and the reagent present in the reaction zone is the drug itself and the labelled signal-producing agent is, for example, a gold labelled goat or mouse anti-human antibody, a positive response, indicating the presence of the drug antibody, corresponds to the appearance of color.

In accordance with one aspect of the invention, when the biological fluid being tested is blood, it has been unexpectedly found that whole blood may be directly applied to the surface of the test device without the need for serum separation prior to the sample being applied to the test device. In accordance with this embodiment of the invention, the whole blood sample is applied to the surface of the test device, and then a detergent is applied over the blood sample. While it is known that detergents such as TWEEN (polyoxyethylenesorbitan) may be used to remove red cells and the like from whole blood samples, it has been unexpectedly found that the application of a clearing reagent, such as a detergent (preferably a detergent which includes a mixture of ionic, and nonionic detergents, and an alcohol), allows the application of whole blood to the surface of the assay device without the need to separate the cellular component from the serum prior to application to the device. The application of a detergent is preferable because the detergent disrupts blood cells. The ruptured cell debris then pass through the medium and are removed from the reaction zone, i.e., removed from interfering with immobilized surface antigens.

Once the presence or absence of the analyte has been determined, the detection device made in accordance with the present invention may be used to identify the test subject whose biological fluid was tested. In a preferred embodiment of the invention, determining the identity of the test subject includes performing a ligand-receptor assay which results in the development of a fingerprint of the individual. In accordance with a preferred embodiment of the invention, determining the identity of the test subject is independent of any reactions with the analyte in the fluid.

In accordance with this method of the invention, the person's fingertip is coated with a signal-producing agent conjugated to a MIP. When the coated fingertip is applied to the surface of a control zone, the signal-producing conjugate binds to a MIP embedded in the control zone of the test device. While the invention is not to be limited to a particular theory of operation, it is believed that the ridges and valleys of a person's fingertip provide localized areas of concentrated signal-producing conjugate (corresponding to a valleys) and localized areas of low concentration signal-producing agent (corresponding to a ridge). When applied to the surface of a control zone of a device according to the invention, a clearly identifiable image of a fingerprint is produced, whereby the identity of the person providing the test sample can be provided.

In accordance with the invention, the presence or absence of an analyte of interest in a sample may be determined by applying the sample to the surface of a reaction medium, the reaction medium including at least one reaction zone having a member of an immunological pair therein; and applying a signal-producing agent which binds, directly or indirectly (e.g., a secondary antibody), to the MIP or to the analyte of interest.

The self-contained test device illustrated in FIG. 11 may be used as follows:

A test sample in liquid form, such as a bodily fluid (for example, saliva, urine or blood) is placed on the outer surface of the medium 185 for containing and transferring the test sample. Up to about 20 drops of test sample may be applied to the medium 185. Since this device provides so much greater sensitivity and speed than do conventional test devices, as little as one drop of test sample may be employed preferably, however, about 3 to about 10 drops of test sample are preferably used. With the removable cylindrical member 140 in place in the housing disposed with the open end thereof over the base 128 and signal-producing medium 126 in the first part of the housing 111b, the test sample is applied to the outer surface of the medium 185 or the sample may be applied to the medium and the cylindrical member 140 thereafter placed in housing part 111b. Any analyte which is present in the test sample undergoes reaction with a member of a ligand/receptor pair, preferably a member of an immunological pair, present in lyophilized form in the sponge 185, to form a conjugate. A period of about 1 to about 4 minutes, preferably about 2 minutes, is permitted for incubation (reaction) of the test sample and member of the ligand/receptor pair. With the cylindrical member 140 remaining in place in the second part 111b of the housing, the two parts of housing 111 are brought together to a first closed position in which the outer surface of the sponge 185 contacts the reaction medium 114 and exerts sufficient pressure to transfer substances present in the test sample, the member of the ligand/receptor pair and any conjugate formed between the analyte and the member of the ligand/receptor pair. In this position, although being referred to as a "closed position", the housing may not be entirely closed, depending on the particular structure employed. This closed position is maintained for a period of about 1 to about 4 minutes, preferably about 2 minutes. Thereafter, the housing is opened and the cylindrical member 140, containing the sponge 185 is removed from the housing device. The device is then closed to a fully closed or second closed position in which the signal-producing agent-containing medium 126 contacts the reaction medium 116 with a sufficient pressure to transfer the signal-producing agent, such as a gold-labelled member of a ligand/receptor pair to the reaction medium. The housing is maintained in this second or fully closed position for a period of at least about 5 to about 30 seconds, preferably about 15 seconds.

After about a minute the device will indicate the presence of any analytes being tested for, or an amount of analyte being present in excess of a predetermined concentration or amount, by showing a blank space in the appropriate reaction zone. In most applications, a negative test is reflected by a coloration of the appropriate reaction zone when a specific analyte is absent or is present in amounts where concentration is below a predetermined value. A device will not provide an indication of the identity of the test subject at this stage unless the test subject places a finger or other identifying portion of the body in contact with the control zone 116 of the reaction medium 114 after opening the housing for the second time. Alternatively, rather than applying the finger or other body part to the control zone of the reaction medium after contact has been made between the medium 126 and 114, this step of pressing the two media together may be omitted and the finger or other body part of the test subject may contact under pressure the reaction medium after first being rolled over the signal-producing agent-containing medium 126 or applying the signal-producing agent directly to the finger or other body part with an applicator or dispenser. While each of these methods of identifying the test subject by a permanent and individual characteristic of the test subject is both rapid and sensitive (the total determination typically taking no more than about b 3to 5 minutes), the last described method in which the signal-producing agent is applied directly to the fingertip which is then applied to the reaction medium, is somewhat more effective in that smaller amounts of reagent and sample may be required and the speed of the process is somewhat more rapid. The method in which a finger or other identifying body part is not placed in contact with the reaction medium is least effective in terms of the amounts of material required and speed of the process while contact between the finger or other body part with the transfer medium is intermediate in effectiveness.

Test Kit

In an embodiment of the invention, the assay device made in accordance with the invention may be incorporated into a kit. The kit may also include any of a number of reagents for performing the ligand/receptor assays. For example, the kit may include a test device, at least one agent for producing a signal (or an "ink" pad for transferring the signal-producing agent to the finger), and one or more washing, clearing or detergent reagents. The kit may also include one or more ligands or ligand receptors, such as lyophilized primary antibody and a secondary antibody, and one or more buffers. The ligand or ligand receptor may be a labelled material.

When the compact devices are supplied in kit form, they may be accompanied by a wash bottle containing a phosphate buffer solution. Such wash bottle and/or reagent bottle may be supplied most effectively as a kit with the alternate two-media embodiments of the device of the present invention shown in FIGS. 12 and 13, discussed above. Thus, rather than the device illustrated in FIG. 11 containing a housing and the three media, 114, 126 and 185, a device including a housing and two of the three media, and appropriate reagents contained therein may be employed.

SPECIFIC EXAMPLES

EXAMPLE 1

Figure 3:
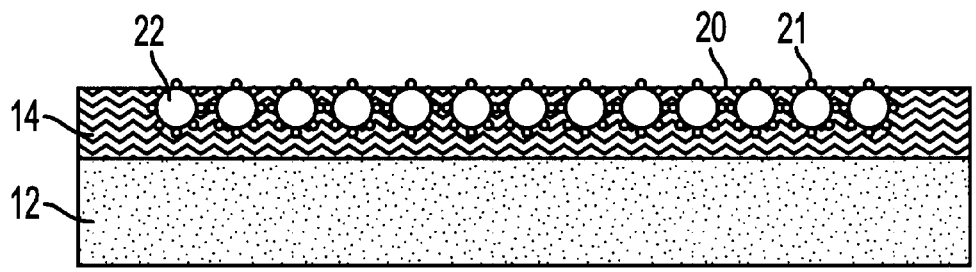
FIG. 3 is an enlarged schematic cross sectional view of an assay device according to the present invention, showing a reaction zone in a reaction medium.
Figure 4:
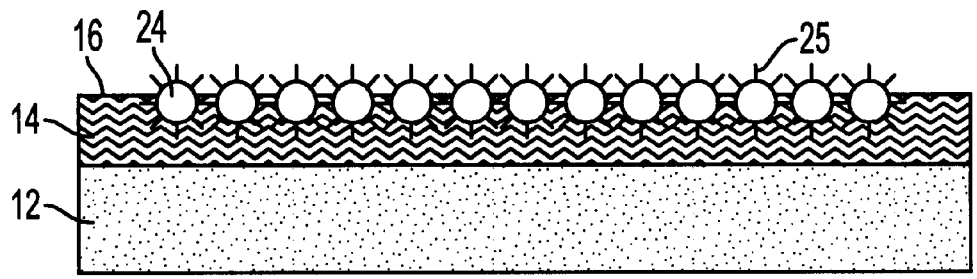
FIG. 4 is an enlarged schematic cross sectional view of an assay device according to the present invention, showing a control zone in a reaction medium.

One embodiment of a immunoassay device of the present invention was prepared according to the following procedure. A reaction zone was constructed by embedding polystyrene particles, coated with human serum albumin-benzoylecgonine (HSA-BE), in one portion of a low protein binding polysulfone membrane (Gelman Supor membrane) mounted on a porous support. A control zone 16 was constructed by embedding polystyrene particles, coated with goat anti-mouse antibody, in a different portion of the membrane. A representative schematic cross section of the reaction and control zones is shown in FIGS. 3 and 4.

The assay device was prepared according to the following procedure. The reaction medium was first rinsed with a blocking buffer solution (Solution A) consisting of 2% polyvinyl alcohol (PVA), 1% glycine and 0.05% TWEEN-20 (polyoxyethylenesorbitan monolaurate) in a phosphate buffered saline solution. The central well of the immunoassay device (control zone 16) was spotted with a dilute solution of polystyrene latex coated with goat anti-mouse immunoglobulin G (adsorbed against human serum) in a phosphate buffered saline containing 4% sucrose, 1.0% BSA and 0.05% azide. The reaction zone was spotted with a dilute solution of polystyrene latex coated with human serum albumin-benzoylecgonine (HSA-BE) in 0.2 M sodium bicarbonate. The reaction medium was then inverted onto hydrophobic polyethylene and dried for one hour in a drying room set between 80 and 100° F. After removal of the reaction medium from the hydrophobic polyethylene, the assay device was ready for use.

EXAMPLE 2

A saliva sample was obtained from a person to be tested for the presence or absence of benzoylecgonine. A 200 microliter aliquot of a dilute solution of mouse anti-benzoylecgonine immunoglobulin G (mouse anti-BE IgG) in a phosphate buffered saline, which contained 0.1% bovine serum albumin (BSA) and 0.05% TWEEN-20, was added to a 200 microliter aliquot of the saliva sample. The resulting mixture was allowed to incubate for three minutes. During this incubation period, 400 microliters of Solution A was added to the reaction medium of the immunoassay device prepared in Example 1 and allowed to drain through the reaction medium. The mouse anti-BE IgG/saliva mixture was then added to the reaction medium and allowed to incubate for two minutes. Another 400 microliter aliquot of Solution A was then added to the reaction medium and allowed to drain. After the Solution A had finished draining, a finger of the person who had provided the saliva sample was painted with 15 microliters of a dilute solution of colloidal gold conjugated goat anti-mouse immunoglobulin G in a TRIS buffer containing 1.0% BSA, 0.05% TWEEN-20 and 0.05% azide (hereinafter "Gold Label Solution"). The finger was gently pressed against the reaction medium of the immunoassay device and held in place for three seconds. The finger was then carefully rolled off the reaction medium. The reaction medium was allowed to incubate for fifteen seconds before another 400 microliter aliquot of Solution A was added to the reaction medium. After completion of the procedure, the reaction zone was colored, showing a negative test result for benzoylecgonine (e.g., as shown with reaction zones $20_1$–$20_3$ in FIG. 2).

The determination was repeated except that a minor amount of benzoylecgonine was added to the saliva sample just prior to the addition of the mouse anti-BE IgG solution. In this instance, after completion of the test, the reaction zones were completely white (e.g., as shown with reaction zones $20_4$–$20_6$ in FIG. 2). At the completion of both determinations, the central well control zone contained an imprint of the finger of the person who had provided the saliva sample (e.g., as shown with the fingerprint 62 on control zone 16 in FIG. 2).

EXAMPLE 3

An immunoassay device is prepared according to the procedure of Example 1 except that the device contains six reaction zones for different analytes. Each reaction zone contains polystyrene particles coated with a different analyte conjugate embedded in the membrane. Reaction zones $20_1$–$20_6$ contain polystyrene latexes coated respectively with cocaine ($20_1$), opiates ($20_2$), PCP ($20_3$), amphetamine/methamphetamine ($20_4$), tetrahydrocannabinol ($20_5$) and alcohol ($20_6$) as the analytes (as shown in FIG. 1). The central control zone 16 is prepared as in Example 1 with polystyrene particles, coated with goat anti-mouse immunoglobulin G, embedded in the membrane.

A saliva sample is obtained from a person to be tested for the presence or absence of the six analytes. A 200 microliter aliquot of a dilute solution of mouse anti-analyte immunoglobulin G for each of the six different analytes in a phosphate buffered saline (hereinafter "mouse anti-analyte IgG Solution I") is added to 200 microliters of the saliva sample. As described in Example 2, while this mixture is incubating, the reaction medium is pretreated with Solution A. After the mouse anti-analyte IgG Solution I/saliva mixture is added to the reaction medium, the remainder of the test procedure described in Example 2 is followed. The reaction medium is treated with Solution A, contacted with a finger of the test subject that has been coated with a dilute solution of colloidal gold conjugated goat anti-mouse immunoglobulin G and then treated again with Solution A. After this procedure is carried out, central control zone 16 contains the imprint of the finger of the person providing the saliva sample. Reaction zones $20_1$–$20_6$ are all colored, showing a negative test result for the presence of all six analytes.

The remaining saliva is then spiked with minor amounts of amphetamine/methamphetamine, tetrahydrocannabinol and alcohol. A 200 microliter aliquot of mouse anti-analyte IgG Solution I is then added to 200 microliters of the spiked saliva and the determination is repeated as described for the unspiked sample. After the procedure is carried out, the assay device exhibits the result shown in FIG. 2. Central control zone 16 contains the imprint of the finger of the person providing the saliva sample. Reaction zones $20_1$–$20_3$ show a negative test result and are colored. Reaction zones $20_4$–$20_6$ show a positive result and are white.

EXAMPLE 4

An immunoassay device, containing six reaction zones, is prepared according to the procedure of Example 1. As in Example 3, reaction zones $20_1$–$20_6$ respectively contain polystyrene latexes coated with cocaine ($20_1$), opiates ($20_2$), PCP ($20_3$), amphetamine/methamphetamine ($20_4$), tetrahydrocannabinol ($20_5$) and alcohol ($20_6$) as the analytes. In this instance, however, the central control zone 16, prepared as in Example 1, contains polystyrene particles coated with mouse goat anti-mouse immunoglobulin G embedded in the membrane. A urine sample is obtained from a person to be tested for the presence or absence of the six analytes. A 200 microliter aliquot of the urine is mixed with 200 microliters of mouse anti-analyte IgG Solution I and the test procedure is then carried out exactly as described in Example 2. After completion of the determination, the central control zone 16 contains the imprint of the finger of the person providing the urine sample and reaction zones $20_1$–$20_6$ are all colored, showing a negative test result for the presence of all six analytes.

The remaining urine is then spiked with minor amounts of amphetamine/methamphetamine, tetrahydrocannabinol and alcohol. A 200 microliter aliquot of mouse anti-analyte IgG Solution I is then added to 200 microliters of the spiked urine and the determination is repeated as described for the unspiked sample. After completion of the determination, the immunoassay device exhibits the result shown in FIG. 2. Central control zone 16 contains the imprint of the finger of the person providing the urine sample. Reaction zones $20_1$–$20_3$ are colored (negative result) and reaction zones $20_4$–$20_6$ are white (positive result).

EXAMPLE 5

Figure 9:
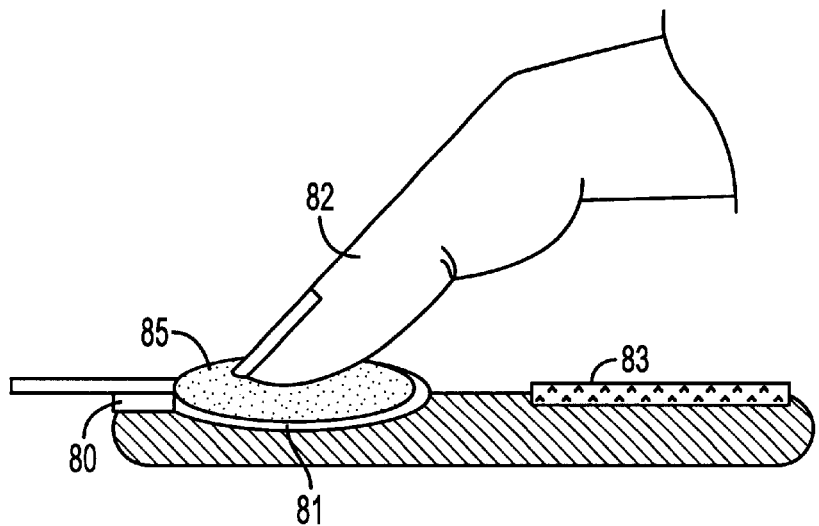
FIG. 9 is an abstract representation of a cross section of an another embodiment of an immunoassay device according to the present invention, illustrating the transfer of a test mixture from a swab to a finger of the person providing the test sample.
Figure 10:
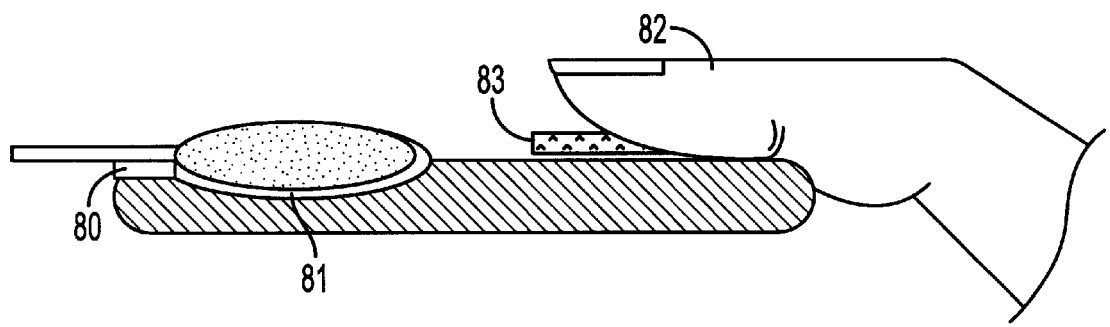
FIG. 10 is an abstract representation of a cross section of the immunoassay device of FIG. 9, illustrating the application of the test mixture to the reaction medium by the finger of the person providing the test sample.

The reaction medium 83 of the immunoassay device shown in FIGS. 9 and 10 is prepared according to the procedure described in Example 1. The reaction medium 83 has six reaction zones $20_1$–$20_6$, which contain polystyrene latexes coated respectively with cocaine ($20_1$), opiates ($20_2$), PCP ($20_3$), methamphetamine ($20_4$), tetrahydrocannabinol ($20_5$) and alcohol ($20_6$) as the analytes and a central control zone 16 containing polystyrene particles, coated with mouse anti-goat immunoglobulin G, embedded in the membrane (as shown in FIGS. 1).

A sterile swab 85 is placed under the tongue of a person whose saliva is to be tested for the presence or absence of the six analytes. After one minute, the swab 85 is removed and is placed in the incubation channel 80 and basin 81 of the immunoassay device (as shown in FIG. 9). Three drops of a dilute solution of silver coated gold microsome conjugates of mouse anti-analyte immunoglobulin G for each of the six different analytes (hereinafter "mouse anti-analyte IgG Solution II") are added to the saliva swab. The treated swab is allowed to incubate for one minute before a finger 82 of the person providing the saliva sample is pressed against the swab for ten seconds. The finger is then lifted off the swab, immediately pressed on the reaction medium of the immunoassay device and held in place for thirty seconds. The finger is then lifted off the reaction medium and the medium is allowed to incubate for two minutes before the result is read. At this, point the central control zone 16 contains the imprint of the finger of the person providing the saliva sample and reaction zones $20_1$–$20_6$ are all colored, showing a negative test result for the presence of all six analytes.

The test procedure is repeated using a new sterile swab except that prior to the addition of the mouse anti-analyte IgG Solution II to the swab, a drop of a solution containing minor amounts of methamphetamine, tetrahydrocannabinol and alcohol is added to the swab. After completion of the test, the immunoassay device exhibits the result shown in FIG. 2. Central control zone 16 contains the imprint of the finger of the person providing the saliva sample. Reaction zones $20_1$–$20_3$ are colored (negative result) and reaction zones $20_4$–$20_6$ are white (positive result).

EXAMPLE 6

An immunoassay device is prepared as in Example 5. A saliva sample is collected from under the tongue of a person to be tested for the presence or absence of the six analytes using a sterile swab. While the saliva sample is being collected, 800 microliters of mouse anti-analyte IgG Solution I is placed in a sample tube together with one drop of a dilute solution of PCP. The saliva-containing swab is allowed to soak in the solution in the sample tube for two minutes. A 400 microliter aliquot of the resulting mixture is applied to the reaction medium and allowed to incubate for twenty seconds. A 400 microliter aliquot of Solution A was then added to the reaction medium and allowed to drain. After the Solution A had finished draining, a finger of the person who had provided the saliva sample is painted with 15 microliters of Gold Label Solution. The finger is immediately pressed gently against the reaction medium of the immunoassay device and held in place for five seconds. After the finger is carefully rolled off the reaction medium, the medium is allowed to incubate for fifteen seconds before another 400 microliter aliquot of Solution A is added to the reaction medium. After the completion of the procedure, the reaction zone is completely white, showing a positive test result for PCP. The central control zone contains an imprint of the finger of the person who had provided the saliva sample.

EXAMPLE 7

An immunoassay device is prepared according to the procedure of Example 1. The reaction medium comprises a nylon membrane. The reaction zone includes polystyrene particles coated with human serum albumin-cocaine embedded in the membrane. The central control zone includes polystyrene particles, coated with goat anti-mouse immunoglobulin G, embedded in the membrane.

A finger of a person to be tested for the presence or absence of cocaine in their blood is pricked with a needle to obtain a droplet of blood. The droplet is spread with a sterile spatula to form a thin film of blood over the fingertip. The blood covered fingertip is pressed against the reaction medium and held in place for about ten seconds. After the finger is lifted off, the reaction medium is treated with a dilute solution of household detergent, thereby removing the red blood color from the reaction medium. After the red blood color has been removed, the reaction medium is treated with a dilute solution of alkaline phosphatase conjugated mouse anti-cocaine immunoglobulin G and allowed to incubate for two minutes. The reaction medium is then treated sequentially with Solution A, a dilute solution of 5-bromo-4-chloro-3-indolyl phosphate and nitroblue tetrazolium (BCIP/NBT) and again with Solution A. The reaction medium is allowed to incubate for several minutes between the BCIP/NBT treatment and the final Solution A treatment. When the procedure is completed, the central control zone contained an imprint of the finger of the person who had provided the blood sample and the reaction zone was colored, showing a negative test result for cocaine.

EXAMPLE 8

An immunoassay device is prepared as in Example 7. A 500 microliter aliquot of a dilute solution of mouse anti-cocaine immunoglobulin G in a phosphate buffered saline containing 0.1% bovine serum albumin (BSA) and 0.05% TWEEN-20 (hereinafter "mouse anti-cocaine IgG Solution"), is placed in a small sample tube. One drop of a solution containing a minor amount of cocaine is added to the sample tube.

A finger of a person to be tested for the presence or absence of cocaine in their blood is pricked with a needle to obtain a droplet of blood and two droplets of blood are added to the mixture in the sample tube. After the resulting mixture is allowed to incubate for two minutes in the sample tube, the mixture is added to the reaction medium of the immunoassay device. The mixture is incubated for one minute on the reaction medium, which is then rinsed with Solution A. A finger of the person who had provided the blood sample is painted with 15 microliters of Gold Label Solution. The finger is gently pressed against the reaction medium of the immunoassay device, held in place for five seconds and then carefully rolled off the reaction medium. The reaction medium is allowed to incubate for fifteen seconds before another 400 microliter aliquot of Solution A is added to the reaction medium. After completion of the procedure, the reaction zone is completely white (positive test for cocaine) and the control zone contains the imprint of the finger of the person providing the blood sample.

EXAMPLE 9

An immunoassay device is prepared according to the procedure of Example 1 except that the device contains six reaction zones (see FIG. 1). Each reaction zone contains polystyrene particles coated with a different amount of cholesterol conjugate embedded in the membrane. Reaction zone $20_1$ contains a cholesterol conjugate which will produce a positive signal when contacted with a biological fluid having greater than or equal to 150 milligram/deciliter total cholesterol level. Reaction zones $20_2$–$20_5$ contain intermediate amounts of cholesterol conjugate, wherein the amount of cholesterol conjugate increases sequentially from zone $20_1$ to zone $20_4$, i.e., 180 mg/dl, 240 mg/dl, 280 mg/dl. The reaction medium also includes two reference control zones corresponding to 30 ml/dl and 65 ml/dl high density lipoprotein.

A finger of a person to be tested for the amount of cholesterol in their blood is pricked with a needle to obtain a droplet of blood. The droplet is added to a small sample tube containing 400 microliters of a dilute solution of mouse anti-cholesterol immunoglobulin G and colloidal gold conjugated mouse anti-cholesterol immunoglobulin G in a phosphate buffered saline containing 0.1% bovine serum albumin (BSA) and 0.05% TWEEN-20 (hereinafter "mouse anti-cholesterol IgG Solution"). After incubation for three minutes, a thin film of the mixture is spread over a fingertip of the person providing the blood sample using a sterile spatula. The fingertip is immediately gently pressed against the reaction medium of the immunoassay device. After holding the finger in place for five seconds, the finger is carefully lifted off the reaction medium. The reaction medium is incubated for one minute and then treated with a dilute solution of household detergent to remove red blood color from the reaction medium. After completion of the procedure, the control zone contains the imprint of the finger of the person providing the blood sample. Reaction zones $20_1$–$20_2$ are colored (negative test for cholesterol), while reaction zones $20_3$ and $20_4$ are white (positive test for cholesterol). Each reaction zone gives a positive test for cholesterol when at least the predetermined threshold amount of cholesterol is present. The threshold cholesterol concentration differs for each reaction zone in correspondence to the amount of cholesterol conjugate adsorbed in the reaction medium in that zone.

EXAMPLE 10

A listing of a number of other drugs, the presence or absence of which may be determined using the present invention follows. This is only exemplary and is not meant to limit the invention thereto.

| ß-Blockers | Diuretics |
| --- | --- |
| Acebutolol | Acetazolamide |
| Alprenolol | Amilonde |
| Atenolol | Bendroflumethiazide |
| Labetalol | Bumetanide |
| Metoprolol | Canrenone |
| Nadolol | Chlormerodrin |
| Oxprenolol | Chlorthalidone |
| Propanolol | Diclofenamide |

-continued

| | |
|---|---|
| Sotalol and related compounds | Ethacrynic acid |
| | Furosemide |
| | Hydrochlorothiazide |
| | Mersalyl |
| | Spironolactone |
| | Triamterene and related compounds |
| Stimulants | Narcotic analgesics |
| Amfepramone | Alphaprodine |
| Amphetamine | Anileridine |
| Amphetaminil | Suprenorphine |
| Amiphenazole | Codeine |
| Benzphetamine | Dextromoramide |
| Caffeine | Dextropropoxyphene |
| Cathine | Diamorphine |
| Chlorphentermine | Dihydrocodeine |
| Clobenzorex | Dipipanone |
| Clorprenaline | Ethoheptazine |
| Cocaine | Ethylmorphine |
| Cropropamide | Levorphanol |
| Crotethamide | Methadone |
| Dimethamphetamine | Morphine |
| Ephedrine | Nalbuphine |
| Etafedrine | Pentazocine |
| Ethamivan | Pethidine |
| Etilamphetamine | Phenazocine |
| Fencamfamin | Trimeperidine and related compounds |
| Fenethylline | |
| Fenproporex | |
| Furfenorex | |
| Mefenorex | |
| Methamphetamine | |
| Methoxyphenamine | |
| Methylephedrine | |
| Methylphenidate | |
| Morazone | |
| Nikethamide | |
| Pemoline | |
| Pentetrazol | |
| Phendimetrazine | |
| Phenmetrazine | |
| Phentermine | |
| Phenylpropanolamine | |
| Pipradrol | |
| Prolintane | |
| Propylhexedrine | |
| Pyrovalerone | |
| Strychnine and related compounds | |
| Anabolic Steroids | Hallucinogens |
| Bolasterone | Lysergic Acid Diethylamide |
| Boldenone | |
| Clostebol | Mescaline |
| Dehydromethyltestosterone | Phencyclidine (PCP) |
| Fluoxymesterone | Ketamine |
| Mesterolone | 2,5-Dimethoxy-4-Methylamphetamine |
| Methandienone | |
| Methandrostenolone | Tetrahydrocannabinol |
| Methenolone | Marijuana |
| Methyltestosterone | |
| Nandrolone | |
| Norethandrolone | |
| Oxandrolone | |
| Oxymesterone | |
| Oxymetholone | |
| Stanozolol | |
| Testosterone and related compounds | |
| Opiates | Sedatives/Hypnotics |
| Heroin | Chloral Hydrate |
| Morphine | Glutethimide |
| Methandone | Meprobamate |
| Meperidine | Methaqualone |
| Codeine | |
| Propoxyphene | |

| | |
|---|---|
| Barbiturates | Benzodiazepines |
| Amobarbital | Diazepam |
| Pentobarbital | Clorazepate |
| Secobarbital | Chlordiazepoxide |
| Phenobarbital | Oxazepam |
| Butalbital | Flurazepam |
| Butabartial | Lorazepam |
| | Alprazolam |
| Antipsychotics/ Antidepressants | Solvents |
| | Ethanol |
| Chlorpromazinc | Methanol |
| Trazodone | Isopropanol |
| Haloperidol | Ethylene Glycol |
| Amoxapine | Chloroform |
| Lithium Carbonate | |
| Imipramine | |
| Analgesics | Anabolic Steroids |
| Acetylsalicylic Acid | Testosterone |
| Acetaminophen | Methyltesiosterone |
| Ibuprofen | Nandrolone |
| Diflunisal | Stanozolol |
| Phenylbutazone | Oxandrolone |
| | Methandrostenolone |
| | Clostebol |
| | Mesterolone |
| | Norethandrolone |

EXAMPLE 11

The following table sets forth exemplary chromogenic substrates yielding water-insoluble products that may be used with an appropriate enzyme conjugate in the invention, instead of the colloidal gold label previously noted. Labeling methods utilizing enzyme/chromogen couples are well known and would be easily practiced by one skilled in the art.

Chromogenic Substrates Yielding Water-Insoluble Products

| Enzyme | Substrate | Abbreviation | Orig. Color | Final Color |
|---|---|---|---|---|
| Horseradish Peroxidase | Diaminobenzidene | DAB | Clear | Brown |
| | Diaminobenzidene with nickel enhancement | DAB/nickel | Clear | Grey/Black |
| | 3-Amino-9-ethylcarbazole | AEC | Clear | Red |
| | 4-Chloro-1-naphthol | — | Clear | Blue |
| Alkaline Phosphatase | Naphthol-AS-BI-phosphate/fast red TR | NABP/FR | Clear | Red |
| | Naphthol-AS-MX-phosphate/fast red TR | NAMP/FR | Clear | Red |
| | Naphthol-AS-BI-phosphate/new fuchsin | NABP/NF | Clear | Red |
| | Bromochloroindolyl phosphate/nitro-blue tetrazolium | BCIP/NBT | Clear | Purple |
| | 5-Bromo-4-chloro-3-indolyl-B-d-galactopyranoside | BCIG | Clear | Blue |

-continued

| | Chromogenic Substrates Yielding Water-Insoluble Products | | | |
|---|---|---|---|---|
| Enzyme | Substrate | Abbreviation | Orig. Color | Final Color |
| B-Galactosidase | Naphthol AS-BI-B-d-galactopyranoside | NABG | Clear | Red |

EXAMPLE 12

In this example, the device and method of Example 7 were used, except that the assay device included reaction zones for the analytes, shown in Example 3, the surface of the reaction medium was pre-wetted with Solution A, the test subject's finger was pricked to produce a sufficient quantity of blood to smear the blood over the tip of the subject's finger, and the smeared blood was allowed to dry on the subject's finger. The finger with the dried blood was then applied to the surface of assay device and held in contact with the device for about 15 seconds. After the finger is lifted off, the reaction medium was treated with a dilute solution of clearing reagent, thereby removing the red blood color from the reaction medium. After the red blood color was removed, the reaction medium is treated with a dilute solution of conjugates of colloidal gold bonded to a secondary antibody, each conjugate specifically binding to one of the named analytes. After incubation for about two minutes, a fingertip which had not been used to apply the blood was coated with about 10 microliters of colloidal gold conjugated to a ligand specific for a ligand receptor in the control zone. After the fingertip was removed, the central control zone contained an imprint of the finger of the person who had provided the blood sample and the reaction zone was colored, showing a negative test result for the analytes.

EXAMPLE 13

In this example, the device and method of Example 7 were used, except that the assay device included reaction zones for the analytes, shown in Example 3, the surface of the reaction medium was dry, the test subject's finger was pricked to produce a sufficient quantity of blood to smear the blood over the tip of the subject's finger, and the smeared blood was immediately (before drying) applied to the reaction medium for about 15 seconds. After the finger is lifted off, the reaction medium was allowed to dry (typically about 1 to 2 minutes), treated with a clearing solution to remove the red blood cells, and treated with a dilute solution of clearing reagent, thereby removing the red blood color from the reaction medium. After the red blood color was removed, the reaction medium is treated with a dilute solution of conjugates of colloidal gold bonded to a secondary antibody, each conjugate specifically binding to one of the named analytes. After incubation for about two minutes, a fingertip which had not been used to apply the blood was coated with about 10 microliters of colloidal gold conjugated to a ligand specific for a ligand receptor in the control zone. After the fingertip was removed, the central control zone contained an imprint of the finger of the person who had provided the blood sample and the reaction zone was colored, showing a negative test result for the analytes.

EXAMPLE 14

An assay device, containing five reaction zones (corresponding to areas $20_1$ and $20_3$–$20_6$ in FIG. 1), is prepared according to the procedure of Example 1. As in Example 3, the reaction zones contain polystyrene latexes coated respectively with cocaine ($20_1$), PCP ($20_3$), amphetamine/methamphetamine ($20_4$), tetrahydrocannabinol ($20_5$) and alcohol ($20_6$) as the analytes. In this instance, however, zone $20_2$ does not contain any adsorbed analyte or antibody and serves as a reference control zone, i.e., a zone which will remain completely white at the conclusion of the test. The central control zone ("identity control zone" corresponding to zone 16 in FIG. 1) is prepared as in Example 1, except that it contains polystyrene particles coated with goat anti-rabbit immunoglobulin G embedded in the membrane.

The reaction medium is treated with 500 microliters of Solution A, thereby wetting the reaction medium. A sample of blood is obtained from a test subject to test for the presence or absence of the five analytes in their blood. A portion of the sample is coated on the test subject's fingertip and applied to the five reaction zones and the reference control zone. Pressure is maintained on the reaction medium for about 10–15 seconds.

A few drops, e.g., about a 500 microliter aliquot of a dilute household detergent solution is then added to the reaction medium and allowed to drain. The household detergent treatment lyses any red blood cells present in the reaction medium and rinses the dark red color from the blood out of the medium. The five reaction zones and the reference control zone are then treated with about 10 ml of a dilute solution of a mixture of colloidal gold conjugated mouse anti-analyte immunoglobulin G in a TRIS buffer containing 1.0% BSA, 0.05% TWEEN-20 and 0.05% azide.

A finger of the person who had provided the blood sample is then painted with 15 microliters of a dilute solution of colloidal gold conjugated rabbit anti-goat immunoglobulin G in a TRIS buffer containing 1.0% BSA, 0.05% TWEEN-20 and 0.05% azide. The finger is gently pressed against the identity control zone of the reaction medium and held in place for three seconds. After the finger is carefully lifted off the reaction medium, the medium is allowed to incubate for fifteen seconds before another 400 microliter aliquot of Solution A is added to the reaction medium.

After completion of the procedure, the reaction zones $20_1$ and $20_3$–$20_6$ are colored, showing a negative test result for the analytes. The reference control zone $20_2$ is completely white and the identity control zone contains the imprint of the finger of the person providing the blood sample.

Although the present invention has been described in terms of exemplary embodiment, it is not limited to these embodiments. Alternative embodiments, examples, and modifications which would still be encompassed by the invention may be made by those skilled in the art, particularly in light of the foregoing teachings. Therefore, the following claims are intended to cover any alternative embodiments, examples, modifications, or equivalents which may be included within the spirit and scope of the invention as defined by the claims.

What is claimed is:

1. A self-contained assay device for the detection of an analyte in a test sample provided by a test subject having an identifying body part surface, comprising:

(a) a housing having a first part and a second part, said first and second parts each having an interior surface and an exterior surface, wherein said first and second parts of said housing are movable relative to one another to a first open position and a second closed position;

(b) a reaction medium mounted on the interior surface of said first part of said housing, wherein said reaction medium comprises
  (i) at least one reaction zone comprising a reagent selected from the group consisting of said analyte, a conjugate of said analyte and a protein, an analyte-binding ligand-receptor, and a ligand which binds said analyte-binding ligand-receptor; and
  (ii) optionally, a reference control zone for establishing a reference point in determining the presence or absence of said analyte,
wherein said reaction zone is capable of capturing by specific binding a compound in said test sample medium selected from the group consisting of said analyte and said analyte-binding ligand-receptor;
(c) a signal-producing medium comprising a signal-producing agent which produces a signal in said reaction zone indicative of the presence or absence of said analyte in said test sample, mounted on the interior surface of said second part of said housing,
wherein said reaction medium and said signal-producing medium are mounted and configured such that said signal-producing medium and said reaction medium are in a spaced relationship when said first and second parts of said housing are in said first open position and said signal-producing medium and said reaction medium come into signal-producing agent-transferring contact when said first and second parts of said housing are in said second closed position; and
(d) a removable test sample medium for containing said test sample wherein said removable test sample medium is configured to be positioned intermediate said first and second parts of said housing to come into test sample-transferring contact with said reaction medium when said first and second parts of said housing are in said second closed position;
with the proviso that at least one of said test sample medium and said reaction zone comprises an analyte-binding ligand receptor.

2. The self-contained assay device according to claim 1 wherein said first and second parts of said housing are joined by a hinge.

3. The self-contained assay device according to claim 1 wherein said test sample medium is mounted on one end of a removable cylindrical member which is configured to fit within said first part of said housing in test sample-transferring contact with said reaction medium.

4. The self-contained assay device according to claim 1, wherein said signal-producing medium is a liquid medium.

5. The self-contained assay device according to claim 4, wherein said signal-producing agent is a solution.

6. The self-contained assay device according to claim 4, wherein said signal-producing agent is a colloid.

7. The self-contained assay device according to claim 1, wherein said signal-producing medium is absorbed into a material having lower porosity than said reaction medium and said test sample medium.

8. The self-contained assay device according to claim 7, wherein said signal-producing medium is absorbed into a closed cell polyolefin material.

9. The self-contained assay device according to claim 1, wherein said signal-producing agent produces a visible color change in the absence of analyte.

10. The self-contained assay device according to claim 1, wherein said signal-producing agent produces a visible color change in the presence of analyte.

11. The self-contained assay device according to claim 1, wherein said signal-producing agent is selected from the group consisting of an enzyme, a polymer containing dye, a chemiluminescent agent, a fluorescent agent, a radioisotope, a ferromagnetic particle, a colored particle, and colloidal gold.

12. The self-contained assay device according to claim 11, wherein said signal-producing agent is colloidal gold.

13. The self-contained assay device according to claim 1, wherein said signal-producing agent is bound to an analyte-binding ligand-receptor.

14. The self-contained assay device according to claim 13, wherein said analyte-binding ligand-receptor bound to said signal-producing agent comprises an antibody or fragment thereof capable of specifically binding to said member of a ligand-ligand receptor pair in said identifying control zone.

15. The self-contained assay device according to claim 1, wherein said signal-producing agent-transferring contact occurs at a pressure greater than atmospheric pressure.

16. The self-contained assay device according to claim 1, wherein said signal-producing agent-transferring contact occurs at a pressure of 2 to 15 psi.

17. The self-contained assay device according to claim 1, wherein said removable test sample medium is a sponge.

18. The self-contained assay device according to claim 17, wherein said test sample medium is a fine pored polyester urethane sponge.

19. The self-contained assay device according to claim 1 wherein said test sample-transferring contact occurs at a pressure greater than atmospheric pressure.

20. The self-contained assay device according to claim 1 wherein said test sample-transferring contact occurs at a pressure of 2 to 15 psi.

21. The self-contained assay device according to claim 1, wherein said test sample is a body fluid.

22. The self-contained assay device according to claim 21, wherein said body fluid is selected from the group consisting of saliva, urine, plasma, serum, and blood.

23. The self-contained assay device according to claim 1, wherein said analyte is a compound selected from the group consisting of a drug, a drug metabolite, a drug-protein conjugate, a drug metabolite-protein conjugate, an antibody to a drug, a hapten, an antibody to a hapten, and cholesterol.

24. The self-contained assay device according to claim 23, wherein said analyte is a drug.

25. The self-contained assay device according to claim 1, wherein said reaction medium comprises a reference control zone for establishing a reference point in determining the presence or absence of said analyte.

26. The self-contained assay device according to claim 1, wherein said reference control zone is not capable of capturing by specific binding any compound in said test sample medium.

27. The self-contained assay device according to claim 1, wherein said reagent in said reaction zone comprises said analyte.

28. The self-contained assay device according to claim 1, wherein said reagent comprises a member of an immunological binding pair.

29. The self-contained assay device according to claim 28, wherein said member of an immunological binding pair is an antibody.

30. The self-contained assay device according to claim 1, wherein said reagent is bonded to a carrier material.

31. The self-contained assay device according to claim 1, wherein said reaction medium comprises 6 reaction zones.

32. The self-contained assay device according to claim 1, wherein said reaction medium is physically bonded to a planar support member.

33. The self-contained assay device according to claim 32, wherein said planar support member is a compressible wicking material.

34. The self-contained assay device according to claim 1, wherein said reaction medium comprises a low protein-binding, hydrophilic polysulfone membrane.

35. The self-contained assay device according to claim 1, wherein said reaction medium is layered.

36. The self-contained assay device according to claim 1, wherein said reaction medium contains at least two reaction zones, each reaction zone comprising a reagent for the detection of a different analyte.

37. The self-contained assay device according to claim 1, wherein said reaction medium contains at least two reaction zones, each reaction zone comprising a different concentration of the same reagent.

38. A self-contained assay device for the detection of an analyte in a test sample provided by a test subject having an identifying body part surface, comprising:
  (a) a housing having a first part, a second part and a third part, said first, second and third parts each having an interior surface and an exterior surface;
  (b) a reaction medium mounted on the interior surface of said first part of said housing, wherein said reaction medium comprises
    (i) at least one reaction zone comprising a reagent selected from the group consisting of said analyte, a conjugate of said analyte and a protein, an analyte-binding ligand-receptor and a ligand which binds said analyte-binding ligand receptor, wherein said reaction zone is capable of capturing by specific binding a compound selected from the group consisting of said analyte and said analyte-binding ligand-receptor;
    (ii) an identifying control zone capable of identifying said test subject by imprint of said identifying body part surface, comprising a member of a ligand-ligand receptor pair; and
    (iii) optionally, a reference control zone for establishing a reference point in determining the presence or absence of said analyte;
  (c) a test sample medium for containing said test sample mounted on the interior surface of said second part of said housing, wherein said test sample medium optionally comprises an analyte-binding ligand-receptor, said analyte-binding ligand-receptor optionally being labeled; and
  (d) a signal-producing medium mounted on the interior surface of said third part of said housing, comprising a signal-producing agent which produces a signal in said reaction zone indicative of the presence or absence of said analyte in said test sample;
  wherein said first and second parts of said housing are independently movable between a first open position in which said reaction medium and said test sample medium are in a spaced relationship and a second closed position in which said reaction medium and said test sample medium are brought into test sample-transferring contact, and wherein said first and third parts of said housing are independently movable between a first open position in which said signal-producing medium and said reaction medium are in a spaced relationship and a second closed position in which said signal-producing medium and said reaction medium are brought into signal-producing agent contact,
  with the proviso that at least one of said test sample medium and said reaction zone comprises an analyte-binding ligand-receptor.

39. A self-contained assay device for the detection of an analyte in a test sample provided by a test subject having an identifying body part surface, comprising:
  (a) a housing having a first part and a second part, said first and second parts each having an interior surface and an exterior surface, wherein said first and second parts of said housing are movable relative to one another to a first open position and a second closed position;
  (b) a reaction medium mounted on the interior surface of said first part of said housing, wherein said reaction medium comprises
    (i) at least one reaction zone comprising a reagent selected from the group consisting of said analyte, a conjugate of said analyte and a protein, an analyte-binding ligand-receptor and a ligand which binds to said analyte-binding ligand-receptor;
    (ii) an identifying control zone capable of identifying said test subject by imprint of said identifying body part surface, comprising a member of a ligand-ligand receptor pair; and
    (iii) optionally, a reference control zone for establishing a reference point in determining the presence or absence of said analyte,
  wherein said reaction zone is capable of capturing by specific binding a compound in said test sample selected from the group consisting of said analyte and said analyte-binding ligand-receptor; and
  (c) a signal-producing medium comprising a signal-producing agent which produces a signal in said reaction zone indicative of the presence or absence of said analyte in said test sample, mounted on the interior surface of said second part of said housing;
  wherein said reaction medium and said signal-producing medium are mounted and configured such that said reaction medium and said signal-producing medium are in a spaced relationship when said first and second parts of said housing are in said first open position and said reaction medium and said signal-producing medium come into signal-producing agent transferring contact when said first and second parts of said housing are in said second closed position,
  with the proviso that said reaction zone comprises an analyte-binding ligand receptor.

40. The self-contained assay device according to claim 38 or 39, wherein said analyte is a compound selected from the group consisting of a drug, a drug metabolite, a drug-protein conjugate, a drug metabolite-protein conjugate, an antibody to a drug, a hapten, an antibody to a hapten, and cholesterol.

41. The self-contained assay device according to claim 40, wherein said analyte is a drug.

42. The self-contained assay device according to claim 38 or 39, wherein said signal-producing agent is bound to an analyte-binding ligand-receptor.

43. The self-contained assay device according to claim 42, wherein said analyte-binding ligand-receptor bound to said signal-producing agent comprises an antibody or fragment thereof capable of specifically binding to said member of a ligand-ligand receptor pair in said identifying control zone.

44. The self-contained assay device according to claim 38 or 39, wherein said signal-producing medium is a liquid medium.

45. The self-contained assay device according to claim 38, wherein said signal-producing medium is absorbed into a material having lower porosity than said reaction medium and said test sample medium.

46. The self-contained assay device according to claim 45, wherein said signal-producing medium is absorbed into a closed cell polyolefin material.

47. The self-contained assay device according to claim 38 or 39, wherein said signal-producing agent produces a visible color change in the absence of analyte.

48. The self-contained assay device according to claim 38 or 39, wherein said signal-producing agent produces a visible color change in the presence of analyte.

49. The self-contained assay device according to claim 38 or 39, wherein said signal-producing agent is selected from the group consisting of an enzyme, a polymer containing dye, a chemiluminescent agent, a fluorescent agent, a radioisotope, a ferromagnetic particle, a colored particle, and colloidal gold.

50. The self-contained assay device according to claim 49, wherein said signal-producing agent is colloidal gold.

51. The self-contained assay device according to claim 38 or 39, wherein said signal-producing agent-transferring contact occurs at a pressure greater than atmospheric pressure.

52. The self-contained assay device according to claim 51, wherein said signal-producing agent-transferring contact occurs at a pressure of 2 to 15 psi.

53. The self-contained assay device according to claim 38, wherein said test sample medium is a sponge.

54. The self-contained assay device according to claim 53, wherein said test sample medium is a fine pored polyester urethane sponge.

55. The self-contained assay device according to claim 38, wherein said test sample medium is mounted on one end of a cylinder, wherein the second end of the cylinder removably fits into said housing such that test sample-transferring contact is made between said test sample medium and said reaction medium.

56. The self-contained assay device according to claim 38, wherein said test sample-transferring contact occurs at a pressure greater than atmospheric pressure.

57. The self-contained assay device according to claim 56, wherein said test sample-transferring contact occurs at a pressure of 2 to 15 psi.

58. The self-contained assay device according to claim 38 or 39, wherein said test sample is a body fluid.

59. The self-contained assay device according to claim 58, wherein said body fluid is selected from the group consisting of saliva, urine, plasma, serum, and blood.

60. The self-contained assay device according to claim 38 or 39, wherein said reaction medium comprises a reference control zone for establishing a reference point in determining the presence or absence of said analyte.

61. The self-contained assay device according to claim 60, wherein said reference control zone is not capable of capturing by specific binding any compound in said test sample medium.

62. The self-contained assay device according to claim 38 or 39, wherein said reagent in said reaction zone comprises said analyte.

63. The self-contained assay device according to claim 38 or 39, wherein said reagent comprises a member of an immunological binding pair.

64. The self-contained assay device according to claim 63, wherein said member of an immunological binding pair is an antibody.

65. The self-contained assay device according to claim 38 or 39, wherein said reagent is bonded to a carrier material.

66. The self-contained assay device according to claim 38 or 39, wherein said reaction medium comprises 6 reaction zones.

67. The self-contained assay device according to claim 38 or 39, wherein said reaction medium is physically bonded to a planar support member.

68. The self-contained assay device according to claim 67, wherein said planar support member is a compressible wicking material.

69. The self-contained assay device according to claim 38 or 39, wherein said reaction medium comprises a low protein-binding, hydrophilic polysulfone membrane.

70. The self-contained assay device according to claim 38 or 39, wherein said reaction medium is layered.

71. The self-contained assay device according to claim 38 or 39, wherein said reaction medium contains at least two reaction zones, each reaction zone comprising a reagent for the detection of a different analyte.

72. The self-contained assay device according to claim 38 or 39, wherein said reaction medium contains at least two reaction zones, each reaction zone comprising a different concentration of the same reagent.

73. The self-contained assay device according to claim 38 or 39, wherein said member of a ligand-ligand receptor pair comprises an antispecies antibody.

74. A kit for performing an assay for the detection of an analyte in a test sample provided by a test subject having an identifying body part surface, comprising:

(a) the self-contained assay device according to claim 38;

(b) at least one compound which specifically binds to said analyte, wherein said compound is selected from a ligand and a ligand-receptor; and (c) optionally, a dilute detergent solution.

75. A kit for performing an assay for the detection of an analyte in a test sample provided by a test subject having an identifying body part surface, comprising:

(a) a self-contained assay device comprising a housing having a first part and a second part, said first and second parts each having an interior surface and an exterior surface; a reaction medium mounted on the interior surface of said first part of said housing, wherein said reaction medium comprises (i) at least one reaction zone comprising a reagent selected from the group consisting of said analyte, a conjugate of said analyte and a protein, an analyte-binding ligand-receptor, and a ligand which binds said analyte-binding ligand receptor, wherein said reaction zone is capable of capturing by specific binding a compound selected from the group consisting of said analyte and said analyte-binding ligand-receptor; and (ii) an identifying control zone capable of identifying said test subject by imprint of said identifying body part surface, comprising a member of a ligand-ligand receptor pair, and (iii) optionally, a reference control zone for establishing a reference point in determining the presence or absence of said analyte; a test sample medium for containing said test sample mounted on the interior surface of said second part of said housing, wherein said test sample medium optionally comprises an analyte-binding ligand-receptor, said analyte-binding ligand-receptor optionally being labeled; and (b) a liquid signal-producing medium comprising a signal-producing agent which produces a signal in said reaction zone indicative of the presence or absence of said analyte in said test sample; and (c) optionally, a dilute detergent solution, wherein said first and second parts of said housing are independently movable between a first open position in which said reaction medium and said test sample medium are in a spaced relationship and a second closed position in which said reaction medium and said test sample medium are brought into test sample-transferring contact, with the proviso that at least one of said test sample medium and said reaction zone comprises an analyte-binding ligand-receptor.

76. The kit according to claim 75, further comprising an applicator for said signal-producing medium.

77. The kit according to claim 76, wherein said applicator is a spatula.

78. The kit according to claim 76, wherein said applicator is a swab.

79. The kit according to claim 76, wherein said applicator is a dropper bottle.

* * * * *